US012767727B2

(12) United States Patent
Stewart et al.

(10) Patent No.: US 12,767,727 B2
(45) Date of Patent: Oct. 20, 2026

(54) ANTI-CD73 ANTIBODIES

(71) Applicant: CANCER RESEARCH TECHNOLOGY LIMITED, London (GB)

(72) Inventors: Lorna Stewart, Cambridge (GB); Grainne Gernon, Cambridge (GB); Zoë Johnson, Geneva (CH); Marcel Deken, Geneva (CH)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 410 days.

(21) Appl. No.: 18/285,996

(22) PCT Filed: Apr. 8, 2022

(86) PCT No.: PCT/EP2022/059489
§ 371 (c)(1),
(2) Date: Oct. 6, 2023

(87) PCT Pub. No.: WO2022/214677
PCT Pub. Date: Oct. 13, 2022

(65) Prior Publication Data

US 2024/0117065 A1 Apr. 11, 2024

(30) Foreign Application Priority Data

Apr. 9, 2021 (GB) ..................................... 2105110

(51) Int. Cl.

| | |
|---|---|
| ***C07K 16/28*** | (2006.01) |
| ***A61K 38/00*** | (2006.01) |
| ***A61K 39/395*** | (2006.01) |
| ***A61P 35/00*** | (2006.01) |
| ***C12N 15/63*** | (2006.01) |

(52) U.S. Cl.
CPC .......... *C07K 16/2896* (2013.01); *A61K 38/00* (2013.01); *A61P 35/00* (2018.01); *C12N 15/63* (2013.01); *C07K 2317/565* (2013.01); *C07K 2317/76* (2013.01)

(58) Field of Classification Search
None
See application file for complete search history.

(56) References Cited

U.S. PATENT DOCUMENTS

2021/0070876 A1 3/2021 Grandal et al.

FOREIGN PATENT DOCUMENTS

| | | | |
|---|---|---|---|
| CN | 112574313 | A | 3/2021 |
| EP | 3556773 | A1 | 10/2019 |
| EP | 3569618 | A1 | 11/2019 |
| WO | 2016/075099 | A1 | 5/2016 |
| WO | 2018215535 | A1 | 11/2018 |
| WO | 2019/173291 | A1 | 9/2019 |
| WO | 2019/232244 | A2 | 12/2019 |
| WO | 2020/098599 | A1 | 5/2020 |
| WO | 2021/017892 | A1 | 2/2021 |

OTHER PUBLICATIONS

Chen et al. (2019) "CD73: An Emerging Checkpoint for Cancer Immunotherapy" Immunotherapy 11(11): 983-997.*
Roh et al. (2020) "Targeting CD73 to augment cancer immunotherapy" Current Opinion in Pharmacology 53: 66-76.*
International Search Report and Written Opinion issued for Application No. PCT/EP2022/059489, dated Aug. 3, 2022. 20 pages.

* cited by examiner

*Primary Examiner* — Ilia I Ouspenski
(74) *Attorney, Agent, or Firm* — Meunier Carlin & Curfman LLC

(57) ABSTRACT

This invention relates to anti-CD73 antibody molecules that include a VH domain comprising a VHCDR1 of SEQ ID NO: 1, a VHCDR2 of SEQ ID NO: 2, and a VHCDR3 of SEQ ID NO: 3; and a VL domain comprising a VLCDR1 of SEQ ID NO: 4, a VLCDR2 of SEQ ID NO: 5, and a VLHCDR3 of SEQ ID NO: 6. Antibody molecules and methods for their production and use in therapy, for example for treating cancer or reducing tumor-mediated immunosuppression are provided.

18 Claims, 4 Drawing Sheets

Specification includes a Sequence Listing.

SEQUENCE LISTING

<160> NUMBER OF SEQ ID NOS: 26

<210> SEQ ID NO 1
<211> LENGTH: 5
<212> TYPE: PRT
<213> ORGANISM: Artificial Sequence
<220> FEATURE:
<223> OTHER INFORMATION: Heavy chain variable complementarity determining region 1
<220> FEATURE:
<221> NAME/KEY: MISC_FEATURE
<222> LOCATION: (3)..(3)
<223> OTHER INFORMATION: Xaa = Y or A

<400> SEQUENCE: 1

Asp Tyr Xaa Met Ser
1 5

<210> SEQ ID NO 2
<211> LENGTH: 17
<212> TYPE: PRT
<213> ORGANISM: Artificial Sequence
<220> FEATURE:
<223> OTHER INFORMATION: Heavy chain variable complementarity determining region 2

<400> SEQUENCE: 2

Tyr Ile Ser Ser Ser Ser Ser Tyr Thr Asn Tyr Ala Asp Ser Val Lys
1 5 10 15

Gly

<210> SEQ ID NO 3
<211> LENGTH: 8
<212> TYPE: PRT
<213> ORGANISM: Artificial Sequence
<220> FEATURE:
<223> OTHER INFORMATION: Heavy chain variable complementarity determining region 3
<220> FEATURE:
<221> NAME/KEY: MISC_FEATURE
<222> LOCATION: (2)..(2)
<223> OTHER INFORMATION: Xaa = Y, F, A or W

<400> SEQUENCE: 3

Gly Xaa Tyr Gln Tyr Phe Asp Tyr
1 5

<210> SEQ ID NO 4
<211> LENGTH: 13
<212> TYPE: PRT
<213> ORGANISM: Artificial Sequence
<220> FEATURE:
<223> OTHER INFORMATION: Light chain variable complementarity determining region 1
<220> FEATURE:
<221> NAME/KEY: MISC_FEATURE
<222> LOCATION: (4)..(4)
<223> OTHER INFORMATION: Xaa = R or S
<220> FEATURE:
<221> NAME/KEY: MISC_FEATURE
<222> LOCATION: (9)..(9)
<223> OTHER INFORMATION: Xaa = H or S
<220> FEATURE:
<221> NAME/KEY: MISC_FEATURE
<222> LOCATION: (13)..(13)
<223> OTHER INFORMATION: Xaa = S or Y

<400> SEQUENCE: 4

Ser Gly Ser Xaa Ser Asn Ile Gly Xaa Asn Tyr Val Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Light chain variable complementarity
      determining region 2
<220> FEATURE:
<221> NAME/KEY: MISC_FEATURE
<222> LOCATION: (1)..(1)
<223> OTHER INFORMATION: Xaa = D or R
<220> FEATURE:
<221> NAME/KEY: MISC_FEATURE
<222> LOCATION: (3)..(3)
<223> OTHER INFORMATION: Xaa = D or N
<220> FEATURE:
<221> NAME/KEY: MISC_FEATURE
<222> LOCATION: (4)..(4)
<223> OTHER INFORMATION: Xaa = K or Q

<400> SEQUENCE: 5

Xaa Asn Xaa Xaa Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Light chain variable complementarity
      determining region 3
<220> FEATURE:
<221> NAME/KEY: MISC_FEATURE
<222> LOCATION: (3)..(3)
<223> OTHER INFORMATION: Xaa =  Y, F, A or W
<220> FEATURE:
<221> NAME/KEY: MISC_FEATURE
<222> LOCATION: (5)..(5)
<223> OTHER INFORMATION: Xaa =  D, E or A
<220> FEATURE:
<221> NAME/KEY: MISC_FEATURE
<222> LOCATION: (6)..(6)
<223> OTHER INFORMATION: Xaa =  S, T or A
<220> FEATURE:
<221> NAME/KEY: MISC_FEATURE
<222> LOCATION: (8)..(8)
<223> OTHER INFORMATION: Xaa = N, S, Q or A

<400> SEQUENCE: 6

Ala Ala Xaa Asp Xaa Xaa Leu Xaa Gly Trp Val
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Heavy chain variable complementarity
      determining region 1 (H07)

<400> SEQUENCE: 7

Asp Tyr Ala Met Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Heavy chain variable complementarity determining region 1 (germlined H07 variant)

<400> SEQUENCE: 8

Asp Tyr Tyr Met Ser
1 5

<210> SEQ ID NO 9
<211> LENGTH: 8
<212> TYPE: PRT
<213> ORGANISM: Artificial Sequence
<220> FEATURE:
<223> OTHER INFORMATION: Heavy chain variable complementarity determining region 3 (H07)

<400> SEQUENCE: 9

Gly Trp Tyr Gln Tyr Phe Asp Tyr
1 5

<210> SEQ ID NO 10
<211> LENGTH: 13
<212> TYPE: PRT
<213> ORGANISM: Artificial Sequence
<220> FEATURE:
<223> OTHER INFORMATION: Light chain variable complementarity determining region 1 (H07)

<400> SEQUENCE: 10

Ser Gly Ser Arg Ser Asn Ile Gly His Asn Tyr Val Ser
1 5 10

<210> SEQ ID NO 11
<211> LENGTH: 13
<212> TYPE: PRT
<213> ORGANISM: Artificial Sequence
<220> FEATURE:
<223> OTHER INFORMATION: Light chain variable complementarity determining region 1 (germlined H07 variant)

<400> SEQUENCE: 11

Ser Gly Ser Ser Ser Asn Ile Gly Ser Asn Tyr Val Tyr
1 5 10

<210> SEQ ID NO 12
<211> LENGTH: 7
<212> TYPE: PRT
<213> ORGANISM: Artificial Sequence
<220> FEATURE:
<223> OTHER INFORMATION: Light chain variable complementarity determining region 2 (H07)

<400> SEQUENCE: 12

Asp Asn Asp Lys Arg Pro Ser
1 5

<210> SEQ ID NO 13
<211> LENGTH: 7
<212> TYPE: PRT
<213> ORGANISM: Artificial Sequence
<220> FEATURE:
<223> OTHER INFORMATION: Light chain variable complementarity determining region 2 (germlined H07 variant)

<400> SEQUENCE: 13

Arg Asn Asn Gln Arg Pro Ser
1 5

<210> SEQ ID NO 14
<211> LENGTH: 11
<212> TYPE: PRT
<213> ORGANISM: Artificial Sequence
<220> FEATURE:
<223> OTHER INFORMATION: Light chain variable complementarity determining region 3 (modified H07)
<220> FEATURE:
<221> NAME/KEY: MISC_FEATURE
<222> LOCATION: (3)..(3)
<223> OTHER INFORMATION: Xaa = Y, F, A or W

<400> SEQUENCE: 14

Ala Ala Xaa Asp Asp Ser Leu Asn Gly Trp Val
1 5 10

<210> SEQ ID NO 15
<211> LENGTH: 11
<212> TYPE: PRT
<213> ORGANISM: Artificial Sequence
<220> FEATURE:
<223> OTHER INFORMATION: Light chain variable complementarity determining region 3 (modified germlined H07 )
<220> FEATURE:
<221> NAME/KEY: MISC_FEATURE
<222> LOCATION: (3)..(3)
<223> OTHER INFORMATION: Xaa = Y, F, A or W

<400> SEQUENCE: 15

Ala Ala Xaa Asp Asp Ser Leu Ser Gly Trp Val
1 5 10

<210> SEQ ID NO 16
<211> LENGTH: 11
<212> TYPE: PRT
<213> ORGANISM: Artificial Sequence
<220> FEATURE:
<223> OTHER INFORMATION: Light chain variable complementarity determining region 3 (H07)

<400> SEQUENCE: 16

Ala Ala Trp Asp Asp Ser Leu Asn Gly Trp Val
1 5 10

<210> SEQ ID NO 17
<211> LENGTH: 117
<212> TYPE: PRT
<213> ORGANISM: Artificial Sequence
<220> FEATURE:
<223> OTHER INFORMATION: Heavy chain variable
<220> FEATURE:
<221> NAME/KEY: MISC_FEATURE
<222> LOCATION: (1)..(1)
<223> OTHER INFORMATION: Xaa = Q or E
<220> FEATURE:
<221> NAME/KEY: MISC_FEATURE
<222> LOCATION: (13)..(13)
<223> OTHER INFORMATION: Xaa = Q or K
<220> FEATURE:
<221> NAME/KEY: MISC_FEATURE
<222> LOCATION: (30)..(30)
<223> OTHER INFORMATION: Xaa = G or S
<220> FEATURE:
<221> NAME/KEY: MISC_FEATURE
<222> LOCATION: (33)..(33)
<223> OTHER INFORMATION: Xaa = A or Y
<220> FEATURE:
<221> NAME/KEY: MISC_FEATURE
<222> LOCATION: (37)..(37)
<223> OTHER INFORMATION: Xaa = I or F
<220> FEATURE:
<221> NAME/KEY: MISC_FEATURE
<222> LOCATION: (75)..(75)
<223> OTHER INFORMATION: Xaa = S or A
<220> FEATURE:
<221> NAME/KEY: MISC_FEATURE
<222> LOCATION: (78)..(78)
<223> OTHER INFORMATION: Xaa = T or S
<220> FEATURE:
<221> NAME/KEY: MISC_FEATURE
<222> LOCATION: (100)..(100)
<223> OTHER INFORMATION: Xaa = Y, F, A or W

<400> SEQUENCE: 17

```
Xaa Val Gln Leu Leu Glu Ser Gly Gly Gly Leu Val Xaa Pro Gly Gly
1               5                   10                  15

Ser Leu Arg Leu Ser Cys Ala Ala Ser Gly Phe Thr Phe Xaa Asp Tyr
            20                  25                  30

Xaa Met Ser Trp Xaa Arg Gln Ala Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Xaa Lys Asn Xaa Leu Tyr
65                  70                  75                  80

Leu Gln Met Asn Ser Leu Arg Ala Glu Asp Thr Ala Val Tyr Tyr Cys
                85                  90                  95

Ala Arg Gly Xaa Tyr Gln Tyr Phe Asp Tyr Trp Gly Gln Gly Thr Leu
            100                 105                 110

Val Thr Val Ser Ser
        115
```

<210> SEQ ID NO 18
<211> LENGTH: 117
<212> TYPE: PRT
<213> ORGANISM: Artificial Sequence
<220> FEATURE:
<223> OTHER INFORMATION: Germlined H07 heavy chain variable with modification
<220> FEATURE:
<221> NAME/KEY: MISC_FEATURE
<222> LOCATION: (100)..(100)
<223> OTHER INFORMATION: Xaa = Y, F, A, or W

<400> SEQUENCE: 18

```
Gln Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Xaa Tyr Gln Tyr Phe Asp Tyr Trp Gly Gln Gly Thr Leu
            100                 105                 110
```

```
Val Thr Val Ser Ser
        115


<210> SEQ ID NO 19
<211> LENGTH: 117
<212> TYPE: PRT
<213> ORGANISM: Artificial Sequence
<220> FEATURE:
<223> OTHER INFORMATION: H07 heavy chain variable with modification
<220> FEATURE:
<221> NAME/KEY: MISC_FEATURE
<222> LOCATION: (100)..(100)
<223> OTHER INFORMATION: Xaa = Y, F, A, or W

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Xaa Tyr Gln Tyr Phe Asp Tyr Trp Gly Gln Gly Thr Leu
            100                 105                 110

Val Thr Val Ser Ser
        115


<210> SEQ ID NO 20
<211> LENGTH: 117
<212> TYPE: PRT
<213> ORGANISM: Artificial Sequence
<220> FEATURE:
<223> OTHER INFORMATION: H07 heavy chain variable

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Ser Tyr Ile Ser Ser Ser Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Tyr Gln Tyr Phe Asp Tyr Trp Gly Gln Gly Thr Leu
            100                 105                 110

Val Thr Val Ser Ser
        115


<210> SEQ ID NO 21
<211> LENGTH: 110
<212> TYPE: PRT
```

<213> ORGANISM: Artificial Sequence
<220> FEATURE:
<223> OTHER INFORMATION: Light chain variable
<220> FEATURE:
<221> NAME/KEY: MISC_FEATURE
<222> LOCATION: (26)..(26)
<223> OTHER INFORMATION: Xaa = R or S
<220> FEATURE:
<221> NAME/KEY: MISC_FEATURE
<222> LOCATION: (31)..(31)
<223> OTHER INFORMATION: Xaa = H or S
<220> FEATURE:
<221> NAME/KEY: MISC_FEATURE
<222> LOCATION: (35)..(35)
<223> OTHER INFORMATION: Xaa = S or Y
<220> FEATURE:
<221> NAME/KEY: MISC_FEATURE
<222> LOCATION: (51)..(51)
<223> OTHER INFORMATION: Xaa = D or R
<220> FEATURE:
<221> NAME/KEY: MISC_FEATURE
<222> LOCATION: (53)..(53)
<223> OTHER INFORMATION: Xaa = D or N
<220> FEATURE:
<221> NAME/KEY: MISC_FEATURE
<222> LOCATION: (54)..(54)
<223> OTHER INFORMATION: Xaa = K or Q
<220> FEATURE:
<221> NAME/KEY: MISC_FEATURE
<222> LOCATION: (92)..(92)
<223> OTHER INFORMATION: Xaa = Y, F, A, or W
<220> FEATURE:
<221> NAME/KEY: MISC_FEATURE
<222> LOCATION: (94)..(94)
<223> OTHER INFORMATION: Xaa = D, E or A
<220> FEATURE:
<221> NAME/KEY: MISC_FEATURE
<222> LOCATION: (95)..(95)
<223> OTHER INFORMATION: Xaa = S, T or A
<220> FEATURE:
<221> NAME/KEY: MISC_FEATURE
<222> LOCATION: (97)..(97)
<223> OTHER INFORMATION: Xaa = N, S, Q or A

<400> SEQUENCE: 21

```
Gln Ser Val Leu Thr Gln Pro Pro Ser Ala Ser Gly Thr Pro Gly Gln
1               5                   10                  15

Arg Val Thr Ile Ser Cys Ser Gly Ser Xaa Ser Asn Ile Gly Xaa Asn
            20                  25                  30

Tyr Val Xaa Trp Tyr Gln Gln Leu Pro Gly Thr Ala Pro Lys Leu Leu
        35                  40                  45

Ile Tyr Xaa Asn Xaa Xaa Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Xaa Asp Xaa Xaa Leu
                85                  90                  95

Xaa Gly Trp Val Phe Gly Gly Gly Thr Lys Leu Thr Val Leu
            100                 105                 110
```

<210> SEQ ID NO 22
<211> LENGTH: 110
<212> TYPE: PRT
<213> ORGANISM: Artificial Sequence
<220> FEATURE:
<223> OTHER INFORMATION: Germlined H07 light chain variable with
modification
<220> FEATURE:
<221> NAME/KEY: MISC_FEATURE
<222> LOCATION: (92)..(92)
<223> OTHER INFORMATION: Xaa = Y, F, A, or W

```
<220> FEATURE:
<221> NAME/KEY: MISC_FEATURE
<222> LOCATION: (94)..(94)
<223> OTHER INFORMATION: Xaa = D, E or A
<220> FEATURE:
<221> NAME/KEY: MISC_FEATURE
<222> LOCATION: (95)..(95)
<223> OTHER INFORMATION: Xaa = S, T or A

<400> SEQUENCE: 22

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Xaa Asp Xaa Xaa Leu
                85                  90                  95

Ser Gly Trp Val Phe Gly Gly Gly Thr Lys Leu Thr Val Leu
            100                 105                 110


<210> SEQ ID NO 23
<211> LENGTH: 110
<212> TYPE: PRT
<213> ORGANISM: Artificial Sequence
<220> FEATURE:
<223> OTHER INFORMATION: H07 light chain variable with modification
<220> FEATURE:
<221> NAME/KEY: MISC_FEATURE
<222> LOCATION: (92)..(92)
<223> OTHER INFORMATION: Xaa = Y, F, A, or W
<220> FEATURE:
<221> NAME/KEY: MISC_FEATURE
<222> LOCATION: (94)..(94)
<223> OTHER INFORMATION: Xaa = D, E or A
<220> FEATURE:
<221> NAME/KEY: MISC_FEATURE
<222> LOCATION: (95)..(95)
<223> OTHER INFORMATION: Xaa = S, T or A

<400> SEQUENCE: 23

Gln Ser Val Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly His Asn
            20                  25                  30

Tyr Val Ser Trp Tyr Gln Gln Leu Pro Gly Thr Ala Pro Lys Leu Leu
        35                  40                  45

Ile Tyr Asp Asn Asp Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Xaa Asp Xaa Xaa Leu
                85                  90                  95

Ser Gly Trp Val Phe Gly Gly Gly Thr Lys Leu Thr Val Leu
            100                 105                 110


<210> SEQ ID NO 24
<211> LENGTH: 110
<212> TYPE: PRT
```

<213> ORGANISM: Artificial Sequence
<220> FEATURE:
<223> OTHER INFORMATION: H07 light chain variable

<400> SEQUENCE: 24

Gln Ser Val Leu Thr Gln Pro Pro Ser Ala Ser Gly Thr Pro Gly Gln
1 5 10 15

Arg Val Thr Ile Ser Cys Ser Gly Ser Arg Ser Asn Ile Gly His Asn
20 25 30

Tyr Val Ser Trp Tyr Gln Gln Leu Pro Gly Thr Ala Pro Lys Leu Leu
35 40 45

Ile Tyr Asp Asn Asp Lys Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Ala Ala Trp Asp Asp Ser Leu
85 90 95

Asn Gly Trp Val Phe Gly Gly Gly Thr Lys Leu Thr Val Leu
100 105 110

<210> SEQ ID NO 25
<211> LENGTH: 351
<212> TYPE: DNA
<213> ORGANISM: Artificial Sequence
<220> FEATURE:
<223> OTHER INFORMATION: H07 heavy chain variable

<400> SEQUENCE: 25
gaggtgcagc tgttggagtc tgggggaggc ttggtacagc ctggggggtc cctgagactc 60
tcctgtgcag cctctggatt cacctttggt gattatgcta tgagctggtt ccgccaggct 120
ccagggaagg ggctggagtg ggtttcatac attagtagta gtagtagtta cacaaactac 180
gcagactctg tgaagggccg attcaccatc tccagagaca attccaagaa cacgctgtat 240
ctgcaaatga acagcctgag agccgaggac actgccgtgt attactgtgc gagaggctgg 300
taccaatact ttgactactg gggccagggt acactggtca ccgtgagctc a 351

<210> SEQ ID NO 26
<211> LENGTH: 330
<212> TYPE: DNA
<213> ORGANISM: Artificial Sequence
<220> FEATURE:
<223> OTHER INFORMATION: H07 heavy chain variable

<400> SEQUENCE: 26
cagtctgtgc tgactcagcc accctcagcg tctgggaccc ccgggcagag ggtcaccatc 60
tcatgctctg gaagcaggtc caacatcggg cataactatg tctcctggta tcagcagctc 120
ccaggaacgg cccccaaact cctcatctat gacaatgata agcgaccctc aggggtccct 180
gaccgattct ctggctccaa gtctggcacc tcagcctccc tggccatcag tgggctccgg 240
tccgaggatg aggctgatta ttactgtgca gcatgggatg acagcctgaa tggttgggtg 300
ttcggcggag gaaccaagct gacggtccta 330

ANTI-CD73 ANTIBODIES

CROSS REFERENCE TO RELATED APPLICATIONS

This application is a U.S. national phase application of international patent application number PCT/EP2022/059489 filed on 8 Apr. 2022 and claims priority from GB2105110.7 filed 9 Apr. 2021, the contents and elements of which are herein incorporated by reference for all purposes.

FIELD

The present invention relates to antibodies that specifically bind to Cluster of Differentiation 73 (CD73).

BACKGROUND

Cluster of Differentiation 73 (CD73) is an ecto-5'-nucleotidase encoded by NT5E gene that is ubiquitously expressed in a number of tissues and is frequently overexpressed in the tumour microenvironment where it can be found on tumour-, stromal- and immune cells (Roh et al (2020) Curr Opin Pharmacol 53 66-76).

The CD73 protein is anchored to the cell membrane through a glycosylphosphatidylinositol (GPI) linkage, has ecto-enzyme activity, and plays a role in signal transduction. A soluble form of CD73 can be shed from the membrane through cleavage or hydrolysis of the GPI anchor. CD73, together with CD39, regulates adenosine triphosphate (ATP) metabolism. CD39 (NTPDase-1) converts ATP into AMP, with only trace amounts of ADP being released, while CD73 catalyses the conversion of adenosine monophosphate (AMP) to adenosine and phosphate.

ATP and its metabolites, AMP and adenosine, have important roles in cellular metabolism, immune homeostasis and signalling. Adenosine and ATP are normally present at very low levels in extracellular fluids but inflammation, ischemia, or cancer can lead to the release of high levels of ATP (Leone and Emens (2018) Journal for Immuno Therapy of Cancer 6:57). The release of extracellular ATP in response to cell death or cellular stress acts to activate immune responses, however, its metabolite adenosine has immunosuppressive activity and promotes tumour growth and survival. The accumulation of extracellular adenosine in oncogenic tissues comprises an important mechanism of tumour immune escape by signalling via adenosine receptors on a multitude of immune cells and it has been demonstrated that extracellular adenosine generated by CD73 on tumour cells is sufficient to mediate immune evasion.

Due to the immunosuppressive role of adenosine in the tumour microenvironment CD73 is considered an immune checkpoint and has gained considerable interest as a therapeutic target in cancer (Allard et al (2017) Immunological Reviews 276: 121-144). Elevated CD73 levels in tumour tissues correlate with tumour invasiveness, metastasis, and reduced patient survival time, and thus with poor clinical outcomes (Roh et al (2020) Curr Opin Pharmacol 53 66-76). CD73 has both enzymatic and nonenzymatic functions in cells and both functions of CD73 are involved in cancer associated process. Besides the immune regulation of CD73 by tumour cells, CD73 also affects multiple aspects of tumorigenesis such as proliferation, adhesion/migration, angiogenesis and metastasis. Independent of its enzymatic function, CD73 can also promote cell-to-cell adhesion, migration, invasion of cancer cells as well as stemness.

CD73 expression on tumour cells has been reported in several types of cancer, including colorectal cancer, pancreatic cancer, bladder cancer, leukemia, lymphoma, glioma, glioblastoma, melanoma, ovarian cancer, thyroid cancer, esophageal cancer, prostate cancer, and breast cancer. The majority of CD73 protein in cells exist in a membrane-bound form and is the target of several reported CD73 mAbs. CD73 is expressed on the membrane of different cell types, including vascular endothelial cells (EC) and certain subtypes of lymphocytes as well as tumour and associated stromal cells. CD73 is a signal and adhesive molecule that can regulate cell interaction with extracellular matrix (ECM) components, such as laminin and fibronectin, to mediate cancer invasive and metastatic properties. Continuous recycling of ecto-5'-NT between the cell surface and the intracellular pools has been described, and antibodies targeting CD73 can facilitate internalisation of the molecule, thus removing it from the cell surface and impairing its function.

However, CD73 can be shed from the cell surface, either as a soluble molecule or in form of vesicles, and CD73 activity has been detected in body fluids of patients with inflammation and cancer. Consequently, non-cell-bound and enzymatically active CD73 spreads and modulates the immune response by generating an adenosine-rich anti-inflammatory environment. CD73-containing vesicles of different size and origin and with immunomodulatory function have been found in the tumour microenvironment.

Consequently, antibodies generically referred to as CD73 inhibitors act by modulating certain functions of CD73. For example, one antibody, 7G2 (Life Technologies), has been reported to inhibit CD73 enzymatic activity, however this antibody does not bind cell surface CD73 in flow cytometry, or at best only with very low affinity. Another antibody that binds CD73, clone AD2, has been reported to cause receptor clustering and internalization but has minimal effect on enzymatic activity. A further antibody, 4G4, is reported to induce CD73 shedding from the T cell surface. Yet another antibody is reported to only inhibit soluble CD73 (WO2018215535A1).

A general complicating factor for developing fully human antibodies is that they can have poor pharmacokinetic (PK) profile in preclinical species and can cause hypersensitivity reactions. Poor PK and hypersensitivity reactions severely limit the scope of pharmacology and toxicology studies that need to be performed to fully characterise the antibody before starting clinical trials. A further complication that arises with antibody development is the frequent lack of cross-species specificity. This impairs development timelines and necessitates the need for a "parallel reagent" to prove efficacy and mechanism of action in preclinical (usually rodent) models. Ideally, an antibody will possess cross species reactivity to rodent, primate and human species to allow full characterisation of the antibody intended for clinical development.

In view of the above, there is a need for potent human anti-CD73 antibodies with improved properties, for example anti-CD73 antibodies that block all functions of CD73, are cross reactive with murine systems, have suitable pharmacokinetic (PK) properties and do not cause hypersensitivity reactions in preclinical species.

SUMMARY

The present inventors have developed anti-CD73 antibody molecules that display an unexpectedly favourable combination of properties including one or more of; inhibition of both membrane-bound and soluble CD73 enzymatic activity; internalisation of CD73 from the cell surface upon binding; low affinity for Fcγ receptors; cross reactivity with mouse CD73; pharmacokinetic (PK) properties indicative of serum half-life of greater than 14 days in humans; and reduced hypersensitivity in murine models. The anti-CD73 antibody molecules may be useful in therapy, for example for reducing tumor-mediated immunosuppression.

A first aspect of the invention provides an antibody molecule comprising a VH domain and a VL domain;

wherein the VH domain comprises a VHCDR1 of SEQ ID NO: 1, a VHCDR2 of SEQ ID NO: 2, and a VHCDR3 of SEQ ID NO: 3; and the VL domain comprises a VLCDR1 of SEQ ID NO: 4, a VLCDR2 of SEQ ID NO: 5, and a VLHCDR3 of SEQ ID NO: 6.

The antibody molecule may bind specifically to CD73.

A preferred antibody molecule of the first aspect may for example comprise a VH domain comprising a VHCDR1 of SEQ ID NO: 7, a VHCDR2 of SEQ ID NO: 2, and a VHCDR3 of SEQ ID NO: 9; and a VL domain comprising a VLCDR1 of SEQ ID NO: 10, a VLCDR2 of SEQ ID NO: 12, and a VLCDR3 of SEQ ID NO: 16.

An antibody molecule of the first aspect may comprise a VH domain of SEQ ID NO: 17 and a VH domain of SEQ ID NO: 21. For example, a preferred antibody molecule of the first aspect may comprise a VH domain of SEQ ID NO: 20 and a VL domain of SEQ ID NO: 24.

Preferred antibody molecules of the first aspect are human.

A second aspect of the invention provides a pharmaceutical composition comprising an antibody molecule of the first aspect and a pharmaceutically acceptable carrier.

A third aspect of the invention provides a nucleic acid encoding an antibody molecule of the first aspect or a heavy chain variable domain and/or light chain variable domain thereof.

A fourth aspect of the invention provides a vector comprising a nucleic acid of the third aspect.

A fifth aspect of the invention provides a host cell comprising a nucleic acid of the third aspect or a vector of the fourth aspect.

A sixth aspect of the invention provides a method for making an anti-CD73 antibody molecule, for example, an antibody molecule according to the first aspect, the method comprising expressing, in a host cell culture, a vector according to the fourth aspect to produce said antibody molecule; and recovering the antibody molecule from the cell culture.

A seventh aspect of the invention provides a method of reducing immunosuppression in a tumour and/or inhibiting tumour growth by administering to an individual in need of treatment, an effective amount of an antibody molecule according to the first aspect or the pharmaceutical composition according to the second aspect.

An eighth aspect of the invention provides a method of treatment of cancer by administering, to an individual in need of treatment, an effective amount of an antibody molecule according to the first aspect or the pharmaceutical composition according to the second aspect.

The antibody molecule may be administered alone or in combination with one or more further therapeutic agents in methods of the seventh or eighth aspect.

A ninth aspect of the invention provides an antibody molecule according to the first aspect or the pharmaceutical composition according to the second aspect, for use in therapy and/or a method of treatment of the human or animal body.

A tenth aspect of the invention provides an antibody molecule according to the first aspect or the pharmaceutical composition according to the second aspect, for use in a method of reducing immunosuppression in a tumour and/or inhibiting tumour growth in an individual, for example a method according to the seventh aspect.

An eleventh aspect of the invention provides an antibody molecule according to the first aspect or the pharmaceutical composition according to the second aspect, for use in a method of treatment of cancer in an individual, for example a method according to the eighth aspect.

A twelfth aspect of the invention provides the use of antibody molecule according to the first aspect or a pharmaceutical composition according to the second aspect in the manufacture of a medicament for reducing immunosuppression in a tumour and/or inhibiting tumour growth in an individual, for example in a method according to the seventh aspect.

A thirteenth aspect of the invention provides the use of antibody molecule according to the first aspect or a pharmaceutical composition according to the second aspect in the manufacture of a medicament for the treatment of cancer in an individual, for example in a method according to the eighth aspect.

These and other aspects and embodiments of the invention are described in more detail below.

DETAILED DESCRIPTION

Figure 1:
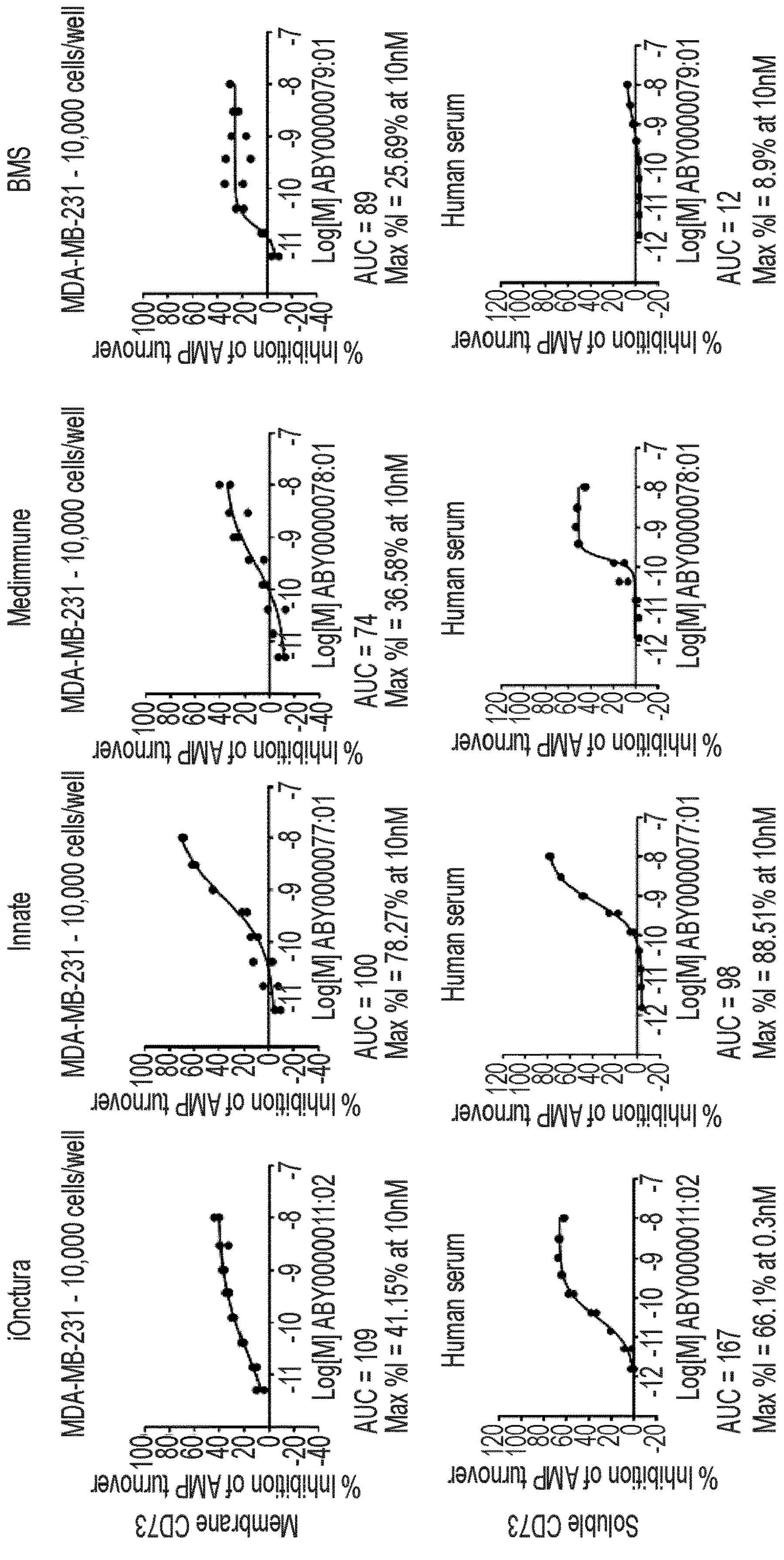
FIG. 1 shows the results of a series of 16-point IC50 screens, which assess the inhibitory effect of IOA-237 and other antibodies against both soluble and membrane-bound CD73 in MDA-MB-231 cells.

This invention relates to the provision of anti-CD73 antibody molecules. The antibody molecules of the invention include a VH domain comprising a VHCDR1 of SEQ ID NO: 1, a VHCDR2 of SEQ ID NO: 2, and a VHCDR3 of SEQ ID NO: 3; and a VL domain comprising a VLCDR1 of SEQ ID NO: 4, a VLCDR2 of SEQ ID NO: 5, and a VLCDR3 of SEQ ID NO: 6.

An antibody molecule described herein may specifically bind to CD73.

An antibody molecule described herein may bind human CD73. Preferably, antibody molecules of the invention are cross reactive with human and mouse CD73. For example, an antibody molecule may bind human CD73 and mouse CD73. Typically, specificity may be determined by means of a binding assay, such as ELISA, employing a panel of antigens.

Cluster of Differentiation 73 (CD73) is an ecto-5'-nucleotidase that converts adenosine monophosphate (AMP) into adenosine and phosphate. CD73 may be soluble or anchored to the cell membrane through a glycosylphosphatidylinositol (GPI) linkage. CD73 is encoded by the gene NT5E (also known as NT, NT5 or CD73). Murine CD73 (Gene ID 23959) may have the reference amino acid sequence NP_035981.1 and may be encoded by the reference nucleic acid sequence NM_011851.4. Human CD73 (Gene ID: 4907) may have the reference amino acid sequence NP_001191742.1 and may be encoded by the reference nucleic acid sequence NM_001204813.2.

An anti-CD73 antibody molecule described herein may display one or more of the following;

(i) inhibition of the ecto-5'-nucleotidase activity (i.e. AMP hydrolysis) of membrane-bound CD73;
(ii) induction of internalisation of membrane-bound CD73 from the cell surface;
(iii) inhibition of the ecto-5'-nucleotidase activity of soluble CD73;
(iv) specific binding to human CD73 and mouse CD73;
(v) no binding to Fcy receptors; and/or
(vi) PK characteristics in mouse indicative of human half-life of at least 14 days.

Preferably, an anti-CD73 antibody molecule described herein displays all of (i) to (vi).

Suitable methods of determining ecto-5'-nucleotidase activity; internalisation of membrane-bound CD73; and binding to CD73 and Fcy receptors are well-established in the art.

An anti-CD73 antibody molecule as described herein may comprise a heavy chain variable (VH) domain and a light chain variable (VL) domain.

The VH domain of an anti-CD73 antibody described herein may comprise the VHCDR1, VHCDR2 and VHCDR3 sequences of SEQ ID NOs 1 to 3, respectively. For example, the VH domain may comprise a VHCDR1 of SEQ ID NO: 7 or SEQ ID NO: 8 and/or a VHCDR3 of SEQ ID NO: 9. In some preferred embodiments, the VH domain of an anti-CD73 antibody described herein may comprise the VHCDR1, VHCDR2 and VHCDR3 sequences of SEQ ID NOs 7, 2 and 9, respectively.

In some embodiments, the VH domain of an anti-CD73 antibody described herein may comprise the VHCDR1, VHCDR2 and VHCDR3 sequences of a VH domain described herein, for example a VH domain of any one SEQ ID NOs: 17 to 20.

The VH domain of an anti-CD73 antibody described herein may comprise the amino acid sequence of SEQ ID NO: 17 or a variant thereof. For example, the VH domain may comprise the amino acid sequence of SEQ ID NO: 18, SEQ ID NO: 19 or a variant of either one of these sequences.

In some embodiments, the VH domain of an anti-CD73 antibody described herein may comprise the amino acid sequence of SEQ ID NO: 20 or a variant thereof; or the amino acid sequence of SEQ ID NO: 20 with independently 1 or more, for example 2, 3, or 4 or more amino acid substitutions, deletions or insertions in the framework regions. The substitutions may be conservative substitutions. In some preferred embodiments, the VH domain of an anti-CD73 antibody described herein may comprise the amino acid sequence of SEQ ID NO: 20.

The VL domain of an anti-CD73 antibody described herein may comprise the VLCDR1, VLCDR2 and VLCDR3 sequences of SEQ ID NOs 4 to 6, respectively. For example, the VL domain may comprise a VLCDR1 of SEQ ID NO: 10 or SEQ ID NO:11; a VLCDR2 of SEQ ID NOL 12 or 13; and/or a VLCDR3 of SEQ ID NO: 14, 15 or 16. In some preferred embodiments, the VL domain of an anti-CD73 antibody described herein may comprise the VHCDR1, VHCDR2 and VHCDR3 sequences of SEQ ID NOs 10, 12 and 16, respectively In some embodiments, the VL domain of an anti-CD73 antibody described herein may comprise the VLCDR1, VLCDR2 and VLCDR3 sequences of a VL domain described herein, for example a VL domain of any one of SEQ ID NOs: 21 to 24.

The VL domain of an anti-CD73 antibody described herein may comprise the amino acid sequence of SEQ ID NO: 21 or a variant thereof. For example, the VH domain may comprise the amino acid sequence of SEQ ID NO: 22, or SEQ ID NO: 23 or a variant of either one of these sequences.

In some embodiments, the VL domain of an anti-CD73 antibody molecule described herein may comprise the amino acid sequence of SEQ ID NO: 24 or a variant thereof; or the amino acid sequence of SEQ ID NO: 24 with independently 1 or more, for example 2, 3, or 4 or more amino acid substitutions, deletions or insertions in the framework regions. The substitutions may be conservative substitutions. In some preferred embodiments, the VL domain of an anti-CD73 antibody described herein may comprise the amino acid sequence of SEQ ID NO: 24.

In some preferred embodiments, an anti-CD73 antibody molecule described herein may comprise a VH domain comprising a VHCDR1 of SEQ ID NO: 7, a VHCDR2 of SEQ ID NO: 2, and a VHCDR3 of SEQ ID NO: 9; and a VL domain comprising a VLCDR1 of SEQ ID NO: 10, a VLCDR2 of SEQ ID NO: 12, and a VLCDR3 of SEQ ID NO: 16. For example, a preferred anti-CD73 antibody molecule may comprise a VH domain of SEQ ID NO: 20 and a VL domain of SEQ ID NO: 24.

A protein described herein that is a variant of a reference sequence, such as a VH or VL domain sequence described herein, may have 1 or more amino acid residues altered relative to the reference sequence. For example, 20 or fewer amino acid residues may be altered relative to the reference sequence, preferably, 15 or fewer, 10 or fewer, 5 or fewer or 3 or fewer, 2 or 1. For example, a variant described herein may comprise the sequence of a reference sequence with 20 or fewer, 15 or fewer, 10 or fewer, 5 or fewer, 3 or fewer, 2 or 1 amino acid residues mutated. For example, a variant described herein may comprise an amino acid sequence with 20 or fewer, 15 or fewer, 10 or fewer, 5 or fewer, 3 or fewer, 2 or 1 amino acid residue altered relative to any one of SEQ ID NOs: 17 to 20, or SEQ ID NOs: 21 to 24. The one or more altered residues are preferably in the framework regions of a VH or VL domain sequence described herein. For example, a variant of a VH or VL domain sequence described herein may comprise a set of VHCDRs 1-3 and VLCDRs 1-3 disclosed herein. A variant of a VH or VL domain sequence described herein may for example comprise 1, 2, 3 or 4 amino acid substitutions in the framework regions.

An amino acid residue in the reference sequence may be altered or mutated by insertion, deletion or substitution, preferably substitution for a different amino acid residue. Such alterations may be caused by one or more of addition, insertion, deletion or substitution of one or more nucleotides in the encoding nucleic acid.

In some embodiments, a variable heavy (VH) or variable light (VL) domain may be reverted to a homologous human germ-line sequence, for example to reduce human immunogenicity and alter amino acid motifs at risk of deamidation (e.g. NG, NS or NT motifs), isomerisation (e.g. DG, DS or DH motifs, cleavage (e.g. DP motif), oxidation (e.g. C or M amino acids), glycosylation or integrin binding. Suitable techniques are known in the art. The closest matching VH germline for the anti-CD73 antibody H07 is the IGHV3-11*03 germ-line (IMGT nomenclature). Reversion to germline may result in 1, 2, 3, 4, 5, 6, or 7 amino acid changes to the VH domain sequence of H07 (3 in FR1, 1 in FR2, 2 in FR3 and 1 in VHCDR1). The closest matching variable light (VL) germline for the anti-CD73 antibody H07 is the IGLV1-47*01. Reversion to germline may result in 1, 2, 3, 4, 5, 6, or 7 amino acid changes to the VH domain sequence of H07 (3 in VLCDR1, 3 in VLCDR2 and 3 in VLCDDR3). A variant of a reference VH or VL domain described herein may include a reversion of the reference sequence to a human germ-line sequence.

In addition, an anti-CD73 VH described here may be chain shuffled with a naïve kappa or lambda light chain population and re-selected against CD73. This may result in an anti-CD73 VH described here being paired with a novel VL partner.

A protein as described herein that is a variant of a reference sequence, such as a VH or VL domain sequence described herein, may share at least 50% sequence identity with the reference amino acid sequence, at least 55%, at least 60%, at least 65%, at least 70%, at least about 80%, at least 90%, at least 95%, at least 98% or at least 99% sequence identity. For example, a variant of a protein described herein may comprise an amino acid sequence that has at least 50% sequence identity with the reference amino acid sequence, at least 55%, at least 60%, at least 65%, at least 70%, at least about 80%, at least 90%, at least 95%, at least 98% or at least 99% sequence identity with the reference amino acid sequence, for example the reference VH domain of SEQ ID NO: 20 or the reference VL domain of SEQ ID NO: 24. Preferably, a variant of a VH domain sequence comprises a set of VHCDRs 1-3 disclosed herein and a variant of a VL domain sequence comprises a set of VLCDRs 1-3 disclosed herein: i.e. sequence variation relative to the reference sequence preferably occurs outside the CDRs, in the framework regions of a variable domain.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) (Altschul et al., 1990), FASTA (which uses the method of Pearson and Lipman (Pearson and Lipman, 1988)), or the Smith-Waterman algorithm (Smith and Waterman, 1981), or the TBLASTN program (Altschul et al., 1990), supra, generally employing default parameters. In particular, the psi-Blast algorithm may be used (Altschul et al., 1997). Sequence identity and similarity may also be determined using Genomequest™ software (Gene-IT, Worcester MA USA).

Sequence comparisons are preferably made over the full-length of the relevant sequence described herein.

The terms "immunoglobulin", "antibody molecule" and "antibody" may be used interchangeably to refer to any protein comprising an antibody antigen-binding site which has the ability to specifically bind one or more antigens.

An "antigen" is an entity (e.g., a proteinaceous entity or peptide) to which an immunoglobulin or antibody (or antigen-binding fragment thereof) specifically binds. The antigens of an anti-CD73 antibody described herein may include soluble or membrane bound CD73 or fragments thereof.

Native antibodies are usually heterotetrameric glycoproteins of about 150,000 Daltons, composed of two identical light (L) chains and two identical heavy (H) chains. Each light chain is linked to a heavy chain by one covalent disulphide bond, with varying numbers of disulphide linkages between the heavy chains of different antibody isotypes. Each heavy and light chain also has regularly spaced intra-chain disulphide bridges.

Antibodies comprise globular regions of heavy or light chain polypeptides called "domains". A domain may comprise peptide loops, usually 3 to 4 loops, which are stabilized, for example, by β-pleated sheet and/or intra-chain disulphide bonding. Domains are generally referred to as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions".

The "constant" domains of an antibody light chain may be referred to as "light chain constant regions", "light chain constant domains", "CL" regions or "CL" domains. The "constant" domains of an antibody heavy chain may be referred to as "heavy chain constant regions", "heavy chain constant domains", "CH" regions or "CH" domains. The constant domain of the light chain is aligned with the first constant domain of the heavy chain. The constant domain of the heavy chain which comprises the tail region of the antibody is referred to herein as the Fc (fragment crystallizable) domain or Fc region. The Fc region may interact with cell surface Fc receptors and some proteins of the complement system, by which method the antibody may activate the immune system. The Fc regions contain three heavy chain constant domains in each polypeptide chain.

The "variable" domains of an antibody light chain may be referred to as "light chain variable regions", "light chain variable domains", "VL" regions or "VL" domains (the 'L' here referring to 'light' rather than the light chain isotype 'lambda'). The "variable" domains of an antibody heavy chain may be referred to as "heavy chain variable regions", "heavy chain variable domains", "VH" regions or "VH" domains. Intact light chains have, for example, two domains (VL and CL) and intact heavy chains have, for example, four or five domains (VH, CH1, CH2, and CH3).

Light and heavy chain variable domains include "hypervariable regions" (HVR or HV), also known as "complementarity determining regions" (CDRs), which are hypervariable in sequence and may form structurally defined loops. Generally, antibodies comprise six hypervariable regions; three in the heavy chain (H1, H2, H3) and three in the light chain (L1, L2, L3) interspersed among relatively conserved framework regions (FRs). In antibodies described herein, the amino acid sequences of the variable domains are shown below. The CDRs may be readily identified in these sequences using standard techniques. The CDRs set out herein are defined in accordance with the Kabat system (Kabat, E. A., Wu, T. T., Perry, H. M., Gottesmann, K. S & Foeller, C. (1991). Sequences of Proteins of Immunological Interest, 5th edit., NIH Publication no. 91-3242. U.S. Department of Health and Human Services). A person skilled in the art is readily able to identify the CDR sequence defined by other systems (e.g. Chothia or AbM) in the VH and VL domains described herein.

The variable regions of each light/heavy chain pair form the antigen binding site. The term "antigen binding site" refers to a site that specifically binds (immunoreacts with) an antigen. Antibodies described herein comprise at least one antigen binding site, preferably comprising two antigen binding sites. An antigen binding site is formed from the heavy and light chain CDRs, aligned by the framework regions, which enable binding to a specific epitope. An "antigen binding region" or "antigen binding domain" is an antibody region or domain that includes an antibody binding site. Antibodies described herein have at least one antigen binding site which recognizes CD73.

Naturally occurring antibody chains or recombinantly-produced antibody chains may be expressed with a leader sequence which is removed during cellular processing to produce a mature chain. Mature chains may also be produced recombinantly, containing a non-naturally occurring leader sequence, for example, to enhance secretion or alter the processing of a particular chain of interest.

The constant regions of the heavy and light chains of an antibody may display phenotypic variation. Antibody light chains are classified as either kappa (κ) or lambda (λ) based on the amino acid sequence of the light chain constant region, and are about 230 residues in length. An antibody described herein comprises a kappa light chain (the variable domain of the kappa light chain is referred to herein as VK). Heavy chains from humans and higher mammals are classified as gamma (γ), mu (μ), alpha (α), delta (δ), or epsilon (E), are about 450-600 residues in length, and define the antibody's isotype as IgG, IgM, IgA, IgD and IgE, respectively. There are two subclasses of IgM (H and L), three subclasses of IgA (IgA1, IgA2, and secretory IgA), and four subclasses of IgG (IgG1, IgG2, IgG3, and IgG4). An antibody described herein is preferably an immunoglobulin G (IgG) antibody, most preferably IgG1.

In some preferred embodiments, an antibody molecule may lack effector function or display reduced effector function. For example, the antibody molecule may be an IgG4 or an IgG1 or IgG2 mutant with reduced or absent Fc effector function.

The antibody molecules described herein may comprise heavy chains which belong to any of the immunoglobulin isotypes described herein. The antibodies described herein may comprise sequences from more than one class or isotype.

An antibody molecule described herein may comprise a fragment of a whole antibody. The term "fragment" refers to a part or portion of an antibody or antibody chain comprising fewer amino acid residues than an intact or complete antibody or antibody chain, wherein the portion preferably retains at least one, preferably most or all, of the functions normally associated with that portion when present in an intact antibody.

Fragments may be obtained via chemical or enzymatic treatment of an intact or complete antibody or antibody chain. Fragments may also be obtained by recombinant means.

Fragments of the antibodies described herein may bind antigen or compete with intact antibody (i.e., with the intact antibody from which they were derived) for antigen binding (i.e., specific binding). Antibodies described herein bind to CD73. Binding fragments are produced by recombinant DNA techniques, or by enzymatic or chemical cleavage of intact immunoglobulins. Antibodies described herein may exist as binding fragments including, but not limited to, Fab, nanobody, Fab', $F(ab')_2$, chemically linked $F(ab')_2$, monospecific $Fab_2$, bispecific $Fab_2$, trispecific $Fab_2$, monovalent IgG, scFv (single-chain variable fragment), di-scFv (divalent scFv), bispecific diabody, TandAb, trispecific triabody, scFv-Fc, Fab-scFv, minibody or sdAb (single domain antibody), mAb2, Fcab, BiTE, CrossMab, κλ-body, DVI-IgG, Duobody, SEEDbody, Knobs in-holes format with a common light chain, DART and other bi-specific formats (see for example Spiess et al., 2015). Suitable fragments retain the ability to bind CD73.

An antibody molecule described herein may be part of a bispecific or trispecific antibody. A bispecific antibody is an artificial hybrid antibody having two different heavy/light chain pairs and two different antigen-binding sites; a trispecific antibody is an artificial hybrid antibody having three different heavy/light chain pairs and three different antigen-binding sites. Bispecific and trispecific antibodies may be produced by a variety of methods including fusion of hybridomas or linking of Fab' fragments. See, e.g., references (Kostelny et al., 1992; Songsivilai and Lachmann, 1990). An exemplary antibody described herein may be a bispecific antibody comprising at least two different antigen binding sites.

Specific binding refers to the situation in which an antibody binds to an epitope on an antigen and will not show any significant binding to molecules other than the specific epitope on the antigen. The term is also applicable where e.g. an antigen binding domain is specific for an epitope which is carried by a number of antigens, in which case the antibody carrying the antigen binding domain will be able to bind to the various antigens carrying the epitope.

Anti-CD73 antibody molecules described herein, or nucleic acids encoding such antibody molecules, will be in an isolated state. Antibody molecules and nucleic acids will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Antibody molecules and nucleic acid may be formulated with diluents or adjuvants and still for practical purposes be isolated—for example the antibodies will normally be mixed with gelatin or other carriers if used to coat microtitre plates for use in immunoassays, or will be mixed with pharmaceutically acceptable carriers or diluents when used in diagnosis or therapy.

Another aspect of the invention provides a nucleic acid which encodes an antibody or a light chain, heavy chain, VH domain or VL domain thereof, as disclosed herein. A nucleic acid may, for example, encode a heavy chain variable domain (VH domain) comprising SEQ ID NO: 17 or a variant thereof, for example a VH domain comprising any one of SEQ ID NOs: 18 to 20 or a variant thereof, and/or a light chain variable domain (VL domain) comprising SEQ ID NO: 21, or a variant thereof, for example a VH domain comprising any one of SEQ ID NOs: 22 to 24 or a variant thereof, as described above. Suitable nucleic acid sequences encoding VH and VL domains are shown in SEQ ID NOs: 25 and 26, respectively. Optionally, the encoded VH domain and/or VL domain may have up to four additional amino acid mutations in the framework region.

The nucleic acids may include DNA and RNA sequences, wherein the thymine nucleobases are substituted with uracil.

Production of the anti-CD73 antibody molecule described herein may be carried out by any suitable technique including techniques described herein as well as other techniques known in the art. Antibodies described herein may be produced on a commercial scale using methods that are well-established in the art for large scale manufacturing of antibodies. For example, recombinant expression systems such as those described herein may be employed.

An antibody molecule described herein may be produced by recombinant expression. Nucleic acids as described above, encoding light and heavy chain variable regions optionally linked to constant regions, may be inserted into expression vectors. Vectors which comprise nucleic acids encoding antibodies described herein are themselves an aspect of the invention. The light and heavy chains may be cloned in the same or different expression vectors. The nucleic acids encoding the antibody chains described herein may be operably linked to one or more control sequences in the expression vector(s) that ensure the expression of the antibody chains. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells (e.g., COS, CHO, or Expi293 cells). Such vectors may be incorporated into an appropriate host, whereby the host is maintained under conditions suitable for high level expression of the nucleotide sequences, and the collection and purification of the antibodies.

Aspects of the invention provide a nucleic acid encoding an anti-CD73 antibody molecule described herein or a VH or VL domain thereof; a vector, preferably an expression vector, comprising one or more nucleic acids that encode an antibody described herein; and a vector comprising one or more nucleic acids that encode an antibody molecule described herein or a VH or VL domain thereof, operably linked to a promoter. Exemplary expression vectors are pHuK and pHuG1 which, in combination with the nucleic acids disclosed herein, comprise nucleotide sequences encoding the antibodies described herein. Other vectors which provide nucleotide sequences encoding the constant regions of antibody light and heavy chains may also be used.

The expression vectors for use as described herein are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al. U.S. Pat. No. 4,704,362).

A vector described herein for use in a eukaryotic host cell may also encode a signal sequence or other polypeptide having a specific cleavage site at the N-terminus of the mature antibody chain or polypeptide. Suitable signal sequences may be heterologous and may be recognized and processed (i.e., cleaved by a signal peptidase) by the host cell. In mammalian cell expression, mammalian signal sequences as well as viral secretory leaders, for example, the herpes simplex gD signal, are available.

Alternatively, antibody-coding sequences described herein may be incorporated into transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or p lactoglobulin.

Vectors described herein containing the polynucleotide sequences of interest (e.g., the heavy and light chain encoding sequences and expression control sequences) may be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Green and Sambrook, Molecular Cloning: A Laboratory Manual (Cold Spring Harbor Press, 4th ed., 2012). Other methods used to transform mammalian cells include the use of polybrene, protoplast fusion, liposomes, electroporation, and microinjection (see generally, Sambrook et al., supra). For production of transgenic animals, transgenes may be microinjected into fertilized oocytes, or may be incorporated into the genome of embryonic stem cells, and the nuclei of such cells transferred into enucleated oocytes.

Host cells may be transformed with the expression vectors and cultured in conventional nutrient media as appropriate for inducing promoters, selecting transformants, and/or amplifying the genes encoding the required sequences. A host cell comprising a nucleic acid or vector described above is provided as an aspect of the invention.

Another aspect of the invention provides a method for making an anti-CD73 antibody molecule described herein, the method comprising expressing, in a host cell culture, a vector described herein to produce said antibody, and recovering the antibody from the cell culture. This method may comprise transferring a vector comprising one or more nucleic acids encoding an anti-CD73 antibody molecule or antibody chains thereof, as described above, into a host cell, as described herein, growing the host cell culture under conditions which allow for expression of the nucleic acid(s) and recovering the expressed anti-CD73 antibody molecule. Any suitable method known in the art may be employed.

Microbial host organisms suitable for use in cloning and expressing the nucleic acids and vectors described herein include prokaryotic hosts; *Escherichia coli*, bacilli, such as *Bacillus subtilis*, and other enterobacteriaceae, such as *Salmonella, Serratia*, and various *Pseudomonas* species. In these prokaryotic hosts, one may also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation. Vectors for use in prokaryotic cells may also require an origin of replication component.

Other microbes, such as yeast, may also be used to express the nucleic acids or vectors described herein. *Saccharomyces* is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express the nucleic acids or vectors described herein and produce the antibody polypeptides (e.g., polynucleotides encoding antibodies or fragments thereof (see e.g, Winnacker, From Genes to Clones, VCH Publishers, N.Y. 1987). A eukaryotic or mammalian cell host comprising a nucleic acid or vector described herein is itself an aspect of the invention. Eukaryotic cells are actually preferred, because a number of suitable host cell lines capable of secreting heterologous proteins (e.g., intact antibodies) have been developed in the art, and include CHO cell lines, various COS cell lines, HeLa cells, Expi293 cells, ExpiCHO cells, myeloma cell lines, or transformed B-cells or hybridomas. The cells may be human or non-human e.g. non-human mammalian cells. In some preferred embodiments, the cells are Expi293 human cells. The antibodies described herein may be produced in cell lines engineered to produce afucosylated proteins, such as the Potelligent® CHOK1SV cell line (BioWa/Lonza), GlymaxX®-engineered cells (ProBioGen) or the duck embryonic stem cell line EB66 (Valneva). Expression vectors for mammalian cells generally include, but are not limited to, one or more of the following: a signal sequence, one or more marker genes, an enhancer element, a promoter, and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like (see for example Co et al., (Co et al., 1992)).

When heavy and light chains are cloned on separate expression vectors, the vectors are co-transfected to obtain expression and assembly of intact antibodies described herein. Once expressed, the whole antibodies, their dimers, individual light and heavy chains, or other immunoglobulin forms described herein may be purified according to standard procedures of the art, including ammonium sulphate precipitation, affinity columns, column chromatography, HPLC purification, gel electrophoresis and the like (see generally Scopes, Protein Purification (Springer-Verlag, N.Y., (1982)). Substantially pure anti-CD73 antibody molecule of at least about 90 to 95% homogeneity are preferred, and 98 to 99% or more homogeneity are most preferred, for pharmaceutical uses as described herein. Standard protein purification methods known in the art may be employed. The following procedures are exemplary of suitable protein purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulphate precipitation, and gel filtration.

An anti-CD73 antibody molecule described herein may specifically bind to human CD73. An antibody described herein may also display the desirable structural, physical, biophysical and chemical properties described below, and with reference to the examples.

The affinity of an anti-CD73 antibody molecule described herein is the extent or strength of binding of antibody to epitope or antigen. The dissociation constant, $K_D$, and the affinity constant, $K_A$, are quantitative measures of affinity. $K_D$ is the ratio of the antibody dissociation rate ($k_{off}$), how quickly it dissociates from its antigen, to the antibody association rate ($k_{on}$) of the antibody, how quickly it binds to its antigen. The binding of an antibody to its antigen is a reversible process, and the rate of the binding reaction is proportional to the concentrations of the reactants. At equilibrium, the rate of [antibody][antigen] complex formation is equal to the rate of dissociation into its components [antibody]+[antigen]. The measurement of the reaction rate constants may be used to define an equilibrium or affinity constant, $K_A$ ($K_A$=1/$K_D$). The smaller the $K_D$ value, the greater the affinity of the antibody for its target. Most antibodies have $K_D$ values in the low micromolar ($10^{-6}$) to nanomolar ($10^{-7}$ to $10^{-9}$) range. High affinity antibodies are generally considered to be in the low nanomolar range ($10^{-9}$) with very high affinity antibodies being in the picomolar ($10^{-12}$) range.

An anti-CD73 antibody molecule described herein may have an association rate constant ($k_{on}$) of at least $10^4$ $Ms^{-1}$, at least $5\times10^4$ $Ms^{-1}$, or at least $10^5$ $M^{-1}$ $s^{-1}$.

An anti-CD73 antibody molecule described herein may have an antibody dissociation ($k_{off}$) rate of less than $10^{-4}$ $s^{-1}$, less than $10^{-5}$ $s^{-1}$, less than $10^{-6}$ $s^{-1}$, or less than $10^{-7}$ $s^{-1}$.

An anti-CD73 antibody molecule described herein may have an equilibrium dissociation constant or $K_D$ from CD73 of less than $5\times10^{-10}$M, less than $10^{-11}$M or less than $10^{-12}$M.

For example, a suitable anti-CD73 antibody may have an association rate constant ($k_{on}$) of at least $10^5$ $M^{-1}$ $s^{-1}$, for example about $1.95\times10^5$ $M^{-1}$ $s^{-1}$, a dissociation ($k_{off}$) rate constant of less than $1\times10^{-7}$ $s^{-1}$ and an equilibrium dissociation constant of $10^{-12}$ M or less.

Specific binding of an anti-CD73 antibody molecule means that the antibody exhibits appreciable affinity for a particular antigen or epitope and, generally, does not exhibit significant cross-reactivity. An antibody that "does not exhibit significant cross-reactivity" is one that will not appreciably bind to an undesirable entity (e.g., an undesirable proteinaceous entity). An antibody specific for a particular epitope will, for example, not significantly cross-react with remote epitopes on the same protein or peptide. Specific binding i.e., $k_{off}$, $k_{on}$, $K_A$ and $K_D$, of an antibody described herein may be determined according to any art-recognized means for determining such binding.

An anti-CD73 antibody molecule disclosed herein may be aglycosylated. The Fc regions of IgG antibodies bear a highly-conserved N-glycosylation site and glycosylation of the Fc fragment is essential for Fc receptor-mediated activity. The N-gly carbohydrate moieties attached to this site are predominantly core-fucosylated diantennary structures of the complex type. In addition, small amounts of these N-glycans also bear bisecting GlcNAc and α-2,6 linked sialic acid residues. An aglycosylated antibody may lack one or more carbohydrate moieties by virtue of, for example, a chemical or enzymatic process, the absence or mutation of one or more glycosylation sites or expression in bacteria. An aglycosylated antibody described herein may be a deglycosylated antibody for which the Fc carbohydrate has been removed, for example, chemically or enzymatically. Alternatively, the aglycosylated antibody described herein may be a nonglycosylated or unglycosylated antibody that was expressed without Fc carbohydrate moieties, for example by mutation of one or more residues that encode the glycosylation pattern or by expression in an organism that does not attach carbohydrates to proteins, for example bacteria.

An anti-CD73 antibody molecule as described herein may be afucosylated, i.e. engineered so that the carbohydrate moieties in the Fc region of the antibody do not have any fucose sugar units. Alternatively, an anti-Aβ antibody disclosed herein may be may have a reduced number of fucose sugar units. Afucosylated antibodies are more effective in antibody-dependent cell-mediated cytotoxicity (see below). Afucosylated antibodies described herein may be produced in cell lines engineered to produce afucosylated proteins, such as the Potelligent® CHOK1SV cell line (BioWa/Lonza), GlymaxX®-engineered cells (ProBioGen) or the duck embryonic stem cell line EB66 (Valneva).

In some embodiment, an anti-CD73 antibody molecule as described herein may be modified to reduce or inhibit its antibody-dependent cell-mediated cytotoxicity (ADCC) and/or complement-dependent cytotoxicity (CDC). For example, an anti-CD73 antibody may comprise an Fc domain that has low effector function, such as an IgG4 effector domain, or an Fc domain that is mutated to eliminate ADCC or CDC activity, such as a mutated IgG1 or IgG2 Fc domain. Suitable mutations are known in the art.

Anti-CD73 antibody molecules may be further modified by chemical modification, for example by PEGylation, or by incorporation in a liposome, to improve their pharmaceutical properties, for example by increasing in vivo half-life.

While it is possible for anti-CD73 antibody molecule, to be administered to the individual alone, it is preferable to present the antibody in a pharmaceutical composition or formulation.

An anti-CD73 antibody molecule described herein may be formulated and/or administered as a pharmaceutical composition comprising the active therapeutic antibody agent and a variety of other pharmaceutically acceptable components, see Remington: The Science and Practice of Pharmacy (22nd ed., Pharmaceutical Press, London, Pa. (2013)). The preferred form depends on the intended mode of administration and therapeutic application. The compositions may also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers and the like.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The formulations may conveniently be presented in unit dosage form and may be prepared by any methods well-known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both.

Pharmaceutical compositions containing an anti-CD73 antibody molecule described herein may also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers may function as immunostimulating agents (i.e., adjuvants).

The anti-CD73 antibody molecule or pharmaceutical composition comprising the anti-CD73 antibody molecule may be administered to a subject by any convenient route of administration, whether systemically/peripherally or at the site of desired action, including but not limited to, oral (e.g. by ingestion); and parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Preferably, an anti-CD73 antibody molecule described herein or a composition comprising an anti-CD73 antibody described herein may be administered intravenously (IV) or subcutaneously (SC), although other routes such as intraperitoneal, intramuscular, transdermal, oral, nasal, or other convenient routes are not excluded The pharmaceutical compositions may be formulated in a dosage unit formulation that is appropriate for the intended route of administration.

For parenteral administration, an antibody or composition described herein may be administered as injectable dosages of a solution or suspension of the substance in a physiologically acceptable diluent with a pharmaceutical carrier that may be a sterile liquid such as water oils, saline, glycerol, or ethanol. Additionally, auxiliary substances, such as wetting or emulsifying agents, surfactants, pH buffering substances and the like may be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies may be administered in the form of a depot injection or implant preparation, which may be formulated in such a manner as to permit a sustained release of the active ingredient.

The term "parenteral" as used herein includes subcutaneous, intravenous, intradermal, intramuscular, intraperitoneal, and intrathecal administration of an antibody or composition described herein. An anti-CD73 antibody or composition described herein may also be administered by nasal or gastric methods. Typically, compositions are prepared as injectables, either as liquid solutions or suspensions; solid forms suitable for solution in, or suspension in, liquid vehicles prior to injection may also be prepared. The preparation also may be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)). The antibody molecules of this invention may be administered in the form of a depot injection or implant preparation, which may be formulated in such a manner as to permit a sustained or pulsatile release of the active ingredient.

Additional formulations suitable for other modes of administration include oral, intranasal, and pulmonary formulations, suppositories, and transdermal applications. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Therapeutic formulations of the anti-CD73 antibody molecule may be prepared for storage by mixing the antibody molecule having the desired degree of purity with optional physiologically acceptable carriers, excipients, or stabilizers (see e.g. "Remington: The Science and Practice of Pharmacy", 20th Edition, 2000, pub. Lippincott, Williams & Wilkins), in the form of lyophilized powder or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

For the anti-CD73 antibody molecule to be used for in vivo administration it must be sterile. This is readily accomplished by filtration through sterile filtration membranes, prior to or following lyophilization and reconstitution. The antibody molecule ordinarily will be stored in lyophilized form or in solution.

Compositions may comprise an anti-CD73 antibody molecule described herein, pharmaceutically acceptable carriers as described herein, and other therapeutic agents, for example prophylactic or therapeutic agents useful for the prevention, management or treatment of cancer conditions.

Compositions described herein may comprise nucleic acids, i.e., DNA or RNA, encoding an anti-CD73 antibody molecule described herein, and any method of delivery of such nucleic acids, with or without any of the other composition compounds discussed above. Compositions may also comprise vectors, for example but not limited to, the expression vectors described herein, themselves comprising the nucleic acids described herein.

Compositions described herein may comprise viral vectors, for use as nucleic acid delivery systems into cells. Suitable viral vector nucleic acid delivery systems include retroviral systems, adenoviral vectors, viral vectors from the pox family including vaccinia virus and the avian pox viruses, and viral vectors from the alpha virus genus. A nucleic acid encoding an antibody described herein, or a vector containing the same, may be packaged into liposomes for delivery to an individual or cell, which may be incorporated into compositions as described. Vectors and nucleic acids encoding an antibody may also be adsorbed to or associated with particulate carriers.

Compositions described herein may comprise gene therapy vectors which contain nucleotide sequences encoding for the antibodies described herein, or naked antibody polypeptide chains according to the invention. Compositions may comprise such vectors or polypeptides in combination with the antibodies described herein, and any other composition components described above.

An anti-CD73 antibody molecule described herein may be used in a kit. The term "kit" is used in reference to a combination of reagents and other materials which facilitate sample analysis. In some embodiments, an immunoassay kit described herein includes a suitable antigen, binding agent comprising a detectable moiety, and detection reagents. A system for amplifying the signal produced by detectable moieties may or may not also be included in the kit. Furthermore, in other embodiments, the kit includes, but is not limited to, components such as apparatus for sample collection, sample tubes, holders, trays, racks, dishes, plates, instructions to the kit user, solutions or other chemical reagents, and samples to be used for standardization, normalization, and/or control samples.

Kits may contain at least one antibody described herein. A kit may comprise a composition described herein, in one or more containers, optionally with one or more other prophylactic or therapeutic agents useful for the prevention, management or treatment of cancer. If the composition containing components for administration is not formulated for delivery via the alimentary canal, such as oral delivery, a device capable of delivering the kit components through some other route may be included, e.g., a syringe. The kit may further include instructions for preventing, treating, managing or ameliorating a cancer condition, as well as side effects and dosage information for method of administration.

Aspects of the invention are also directed to methods of reducing immunosuppression in a tumour and/or inhibiting tumour growth comprising administering to an individual in need of treatment an effective amount of an antibody or composition described herein and antibodies or compositions described herein for use in such methods. This may be useful for example in increasing or promoting anti-cancer immune responses in the individual, for example to counteract cancer cell mediated immune suppression.

Aspects of the invention are also directed to a method of treatment, including prophylaxis, of cancer and other proliferative disorders, by administering to an individual in need of treatment an effective amount of an antibody or composition described herein. An antibody or composition, preferably a pharmaceutical composition (e.g., a composition comprising an antibody described herein, a pharmaceutically acceptable excipient and optionally an additional therapeutic agent) described herein may be for use in a method of treatment of the human or animal body. An antibody or composition, preferably a pharmaceutical composition, described herein may be for use in a method of treatment of the human or animal body, wherein the treatment is therapeutic or prophylactic treatment of a proliferative disorder, such as cancer, in an individual.

In some embodiments, a cancer or other proliferative disorder suitable for treatment as described herein may express CD73 or may express CD73 at an increased level relative to control cells.

Proliferative disorders including cancer and myeloproliferative neoplasms. Cancer suitable for treatment as described herein may be any type of solid or non-solid cancer or malignant lymphoma and especially leukaemia, sarcomas, skin cancer, bladder cancer, breast cancer, uterine cancer, ovarian cancer, prostate cancer, lung cancer, colorectal cancer, cervical cancer, liver cancer, head and neck cancer, oesophageal cancer, pancreatic cancer, renal cancer, stomach cancer and cerebral cancer. Cancers may be familial or sporadic. In some preferred embodiments, the cancer may be a fibrotic cancer such as pancreatic cancer, breast cancer, prostate cancer, and lung cancer.

In some embodiments, the cancer may be pancreatic ductal adenocarcinoma.

The cancer may be a metastatic cancer.

The patient may have been previously identified as having cancer or be at risk of having or at risk of a cancer. A method may comprise identifying the patient as having or at risk of a cancer before administration.

An individual suitable for treatment as described above may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human.

In some preferred embodiments, the individual is a human. In other preferred embodiments, non-human mammals, especially mammals that are conventionally used as models for demonstrating therapeutic efficacy in humans (e.g. murine, primate, porcine, canine, or leporid) may be employed.

In some embodiments, the individual may have minimal residual disease (MRD) after an initial cancer treatment.

An individual with a cancer may display at least one identifiable sign, symptom, or laboratory finding that is sufficient to make a diagnosis of a cancer in accordance with clinical standards known in the art. Examples of such clinical standards can be found in textbooks of medicine such as Harrison's Principles of Internal Medicine, 15th Ed., Fauci A S et al., eds., McGraw-Hill, New York, 2001. In some instances, a diagnosis of a cancer in an individual may include identification of a particular cell type (e.g. a cancer cell) in a sample of a body fluid or tissue obtained from the individual. In some embodiments, the individual may have been previously identified or diagnosed with cancer or a method of the invention may comprise identifying or diagnosing cancer in the individual for example by determining the presence of an identifiable sign, symptom, or laboratory finding indicative of cancer in the individual.

The treatment methods mentioned above may comprise administration of the antibody or composition (e.g., a composition comprising an antibody described herein, a pharmaceutically acceptable excipient and optionally an additional therapeutic agent) described herein to an individual under conditions that generate a beneficial therapeutic response in the individual e.g., for the prevention or treatment of cancer.

An individual suitable for treatment as described herein may be suffering from cancer. The methods of treatment described herein may be used on both asymptomatic patients, and those currently showing symptoms of cancer. An antibody described herein may be administered prophylactically to an individual who does not have cancer. An antibody described herein may be administered to an individual who does not have, or does not exhibit the symptoms of cancer. An antibody described herein may be administered to an individual who does have, or appears to have, cancer. Individuals amenable to treatment include individuals at risk of or susceptible to cancer but not showing symptoms and individuals suspected of having cancer, as well as individuals presently showing symptoms. Antibodies described herein may be administered prophylactically to the general population without the need for any assessment of the risk of the subject individual.

In some embodiments, a cancer suitable for treatment using an anti-CD73 antibody molecule as described herein may comprise cancer cells that express CD73.

The terms "treat", "treating" or "treatment" (or grammatically equivalent terms) mean that the severity of the individual's condition is reduced or at least partially improved or ameliorated and/or that some alleviation, mitigation or decrease in at least one clinical symptom is achieved and/or there is an inhibition or delay in the progression of the condition and/or prevention or delay at the onset of a disease or illness.

An anti-CD73 antibody molecule described herein which may be used in a method of treatment for cancer may be an antibody of any sequence and format described above. The antibody molecule used for methods of treatment as described herein may be fragments of anti-CD73 antibodies described herein, for example antigen binding fragments.

An anti-CD73 antibody molecule described herein may be administered to an individual in need of treatment with a pharmaceutical carrier or pharmaceutical composition, or in any composition described herein.

Alternatively, the anti-CD73 antibody molecule may be administered to an individual by administering a polynucleotide encoding at least one antibody chain. The polynucleotide is expressed to produce the antibody chain in the patient. Optionally, the polynucleotide encodes heavy and light chains of the anti-CD73 antibody molecule. The polynucleotide is expressed to produce the heavy and light chains in the individual.

An anti-CD73 antibody molecule described herein may be used in a method of preventing or treating cancer that involves administering to the patient an effective dosage of the antibody as described herein. As used herein, an "effective amount" or an "effective dosage" or a "sufficient amount" (or grammatically equivalent terms) of a therapeutic antibody described herein refers to an amount of antibody or composition described herein that is effective to produce a desired effect, which is optionally a therapeutic or prophylactic effect (i.e., by administration of a therapeutically effective amount). For example, an "effective amount" or an "effective dosage" or a "sufficient amount" may be an amount so that the severity of the individual's condition, is reduced or at least partially improved or ameliorated and/or that some alleviation, mitigation or decrease in at least one clinical symptom is achieved and/or there is an inhibition or delay in the progression of cancer and/or prevention or delay at the onset of cancer.

Effective doses of the compositions described herein, for the treatment of the above described conditions vary depending upon many different factors, including means of administration, target site, physiological state of the patient, whether the patient is human or an animal, other medications administered, and whether treatment is prophylactic or therapeutic. Usually, the patient is a human but non-human mammals, e.g., non-human primates, rabbits, rats and mice, including transgenic mammals, may also be treated. Treatment dosages need to be titrated to optimize safety and efficacy.

For passive immunization with an antibody described herein, the dosage ranges from about 0.0001 to 100 mg/kg, and more usually 0.01 to 5 mg/kg of the host body weight. For example dosages may be 1 mg/kg body weight or 10 mg/kg body weight or within the range of 1-10 mg/kg, preferably at least 1 mg/kg.

The methods described herein may comprise the administration of an antibody to a subject as a single dose, in two doses, or in multiple doses. The dose of the antibody may be from about 100 μg/kg to 100 mg/kg body weight of the patient. Subjects may be administered such doses daily, on alternative days, weekly or according to any other schedule determined by empirical analysis. A treatment may involve administration in multiple dosages over a prolonged period, for example, of at least six months. Additional treatment regimens may involve administration once per every two weeks or once a month or once every 3 to 6 months.

An anti-CD73 antibody molecule described herein may be administered in combination with one or more other therapeutic agents.

Suitable therapeutic agents for administration in combination with an anti-CD73 antibody molecule described herein may include antibodies specific for: CD39, A2AR, PD-L1, EGFR, PD-1 and CTLA4. Anti-CD73 antibodies may also be administered in combined with small molecule inhibitors or antagonists, such as adenosine A2A receptor inhibitors (A2A/A2BRi), EGFR inhibitors, platinum therapy, radiotherapy, virus or cell-based therapy.

Other aspects and embodiments of the invention provide the aspects and embodiments described above with the term “comprising” replaced by the term “consisting of” and the aspects and embodiments described above with the term “comprising” replaced by the term “consisting essentially of”.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Modifications of the above embodiments, further embodiments and modifications thereof will be apparent to the skilled person on reading this disclosure, and as such, these are within the scope of the present invention.

All documents and sequence database entries mentioned in this specification are incorporated herein by reference in their entirety for all purposes.

The term “and/or” where used herein is to be taken as specific disclosure of each of the two specified features or components with or without the other. For example, “A and/or B” is to be taken as specific disclosure of each of (i) A, (ii) B and (iii) A and B, just as if each is set out individually herein.

EXPERIMENTS

Experiment 1: Generation of Anti-CD73 Antibodies

The n-CoDeR® antibody library contains 30 billion functional human antibody genes (with open reading frame). These antibodies share a common framework structure, and are recombined with different combinations of CDRs to produce novel recombinant antibodies. Candidate antibodies with binding affinity for CD73 were selected using a phage display and the relevant antibody genes were subsequently expressed in *E. coli* bacteria. Chinese Hamster Ovary (CHO) cells were also generated, stably expressing either human CD73 (hCD73) or murine CD73 (mCD73) (Bioinvent international AB) for use in screening assays.

A biopanning strategy to identify anti-CD73 antibody phage was completed in three stages. In the first stage, antibody phage were panned against polymer/streptavidin beads coated with human CD73 (hCD73) or mouse CD73 (mCD73) extracellular domain. In the second stage, antibody phage identified as ‘hits’ against either hCD73/mCD73 in the first stage were pooled, and subject to heterologous panning against polymer/streptavidin beads coated with either hCD73 or mCD73 extracellular domain (i.e., an antibody phage identified as a ‘hit’ against mCD73 in the first stage would be panned against hCD73 in the second stage). This process identifies antibody phage with affinity against both hCD73 and mCD73. In the third stage, antibody phage identified as ‘hits’ in the second stage were re-panned against the same CD73 extracellular domain, or against CHO cells expressing hCD73/mCD73 (i.e., an antibody phage identified as a ‘hit’ against hCD73 in the second stage would be re-panned against hCD73 in the third stage).

Between each stage, candidate antibody phage were additionally assessed for CD73 binding by ELISA (immobilised hCD73/mCD73) or by flow cytometry (CD73-expressing CHO cells). Phage were detected using an anti-M13 antibody.

Following primary screening, 960 candidates were re-assessed for hCD73 and mCD73 binding activity in FMAT (fluorometric microvolume assay technology). In total, 86% of the candidate antibody phage identified in the primary screen were confirmed as hCD73 and mCD73 binders. Of these candidates, 450 clones were taken forward on the basis of high binding affinity for sequencing. A total of 72 unique sequences were identified, suggesting that a number of antibody phage were duplicated in the screens. All sequences were subsequently converted to produce full recombinant IgG antibodies, and 61 of these antibodies were taken forward to assess CD73 inhibitory function.

Experiment 2: Assessing the Inhibitory Function of Candidate Antibodies

The inhibitory function of novel recombinant anti-CD73 antibodies was assessed using a biochemical fluorometric adenosine assay. In brief, antibodies were tested in quadruplicate using a single-point inhibition (IC50) assay at a concentration of 30 μM. Antibodies were considered to successfully inhibit CD73 if their percentage inhibition (%) was greater than mean+3 standard deviations (STD). Catalytically active human/mouse CD73 was purchased from a commercially available source. Of the 61 antibodies selected for analysis, 19 antibodies were identified as successful inhibitors of hCD73 and 11 antibodies were identified as successful inhibitors of mCD73. As such, 8 antibodies were replicated as successful inhibitors of both hCD73 and mCD73, leaving 22 antibodies in total.

These 22 antibodies were subsequently assessed using a 10-point inhibition (IC50) assay. Candidate antibodies were assessed against both hCD73 and mCD73 over concentrations in the range of 0.01-100 μg/mL, and IC50 values were calculated. In summary, the results of this assay support the data previously generated using the single-point assay.

Following IC50 screening, a total of five candidate antibodies were identified as successfully inhibitors of both mCD73 and hCD73, and a lead molecule—antibody IOA-237 (also termed ABY011 or H07)—was selected for further development.

Experiment 3: Assessing the Efficacy of IOA-237 Against Other Antibodies

Comparative studies were completed to assess the inhibitory effect of IOA-237 against other anti-CD73 antibodies. These are: MEDI9447 (MedImmune LLC); BMS-986179 (Bristol-Myers Squibb Pharmaceuticals Limited) and IPH53 (Innate Pharma S.A.).

Percentage inhibition (%) of hCD73 and mCD73 was assessed using a biochemical fluorometric adenosine assay, as previously described. Inhibition of soluble CD73 and membrane-bound CD73 was also assessed in MDA-MB-231 cells, using an equivalent assay. Internalisation of the membrane-bound CD73 receptor was also assessed using a Fab-ZAP internalisation assay kit. As summarised in Table 1, IOA-237 was observed to be a more potent inhibitor of both hCD73 (63.24% inhibition) and mCD73 (50.18% inhibition), as measured in the biochemical assay, when compared to competitor molecules. IOA-237 was also shown to stimulate efficient internalisation of membrane-bound CD73, to a similar extent to MEDI-9447 and BMS-986179 (Table 2). IOA-237 was also shown to stimulate efficient internalisation of membrane-bound CD73, to a similar extent to MEDI9447 and BMS-981679 (Table 2). Furthermore, as measured in the cell-based assay, IOA-237 was observed to inhibit the enzymatic activity of membrane-bound CD73 to an extent similar to that of MEDI9447 (40.72% vs. 42.00%) (Table 3); and soluble CD73 to an extent greater than that of MEDI9447 (61.47% vs. 39.99%).

The inhibitory effect of IOA-237, MEDI9447, BMS-986179 and IPH53 against membrane-bound and soluble CD73 was demonstrated in a series of 16-point IC50 curves (FIG. 1). The increased efficacy of IOA-237 suggests that this novel antibody may be a superior inhibitor of soluble and membrane-bound CD73 when compared to competitor molecules, indicating a potential superior therapeutic utility of IOA-237 for use in oncological indications.

Figure 2:
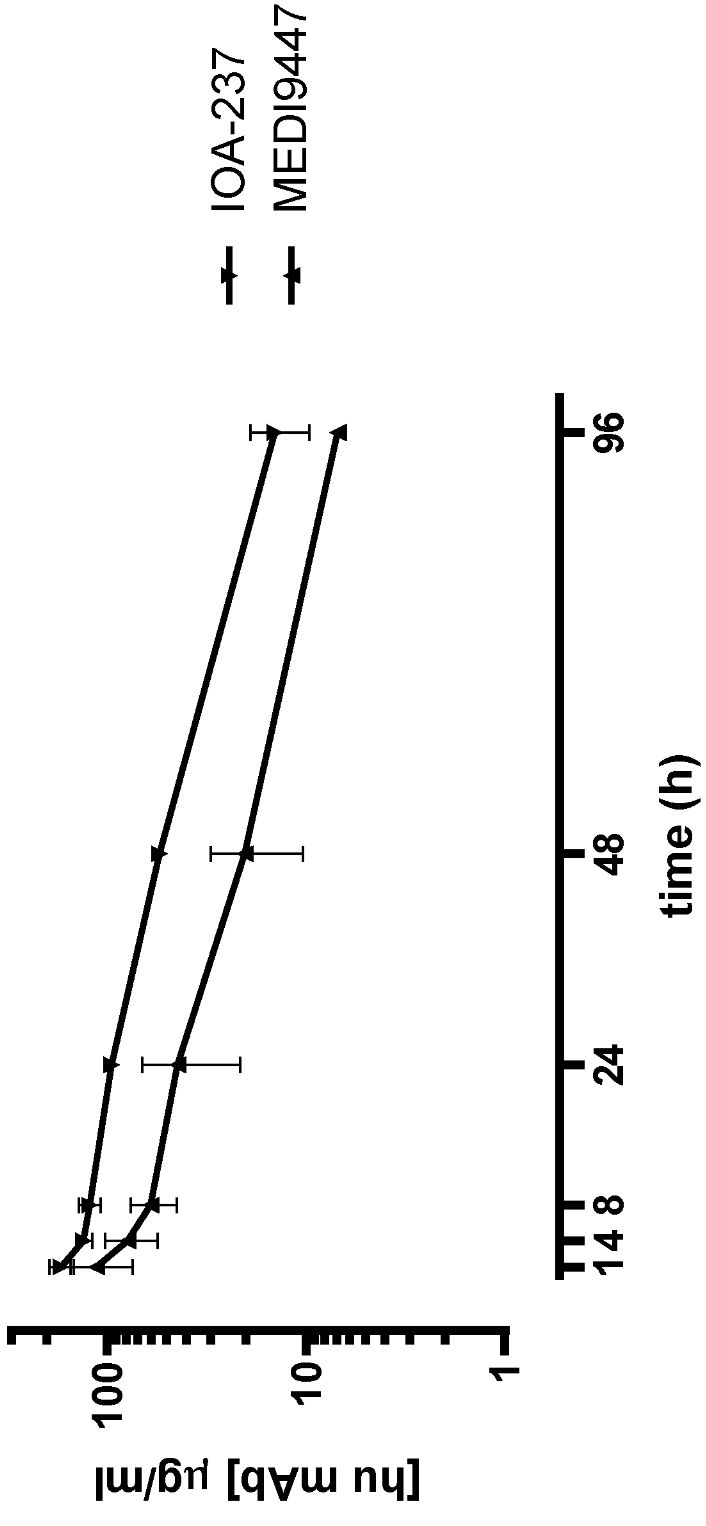
FIG. 2 shows the bioavailability and plasma half-life of IOA-237 in Balb/c mice following intravenous administration in comparison to MEDI-9447, at a dose of 10 mg/kg body weight.

Experiment 4: Assessing the In Vivo Efficacy of IOA-237 in Murine Models of Cancer To assess the pharmacokinetic profile of IOA-237 in vivo, n=3 naïve Balb/c mice were administered IOA-237 or MEDI9447 at a dose of 10 mg/kg body weight. The concentration of antibody was measured in the blood plasma of mice at 1-, 4-, 8-, 24-, 48- and 96-hours post-administration by ELISA. The bioavailability of IOA-237 was found to exceed that of MEDI9447 (FIG. 2). Given the advantageous pharmacokinetic profile of IOA-237 in vivo, the therapeutic utility of IOA-237 for use as an oncolytic agent was assessed in tumour bearing mice.

Figure 3:
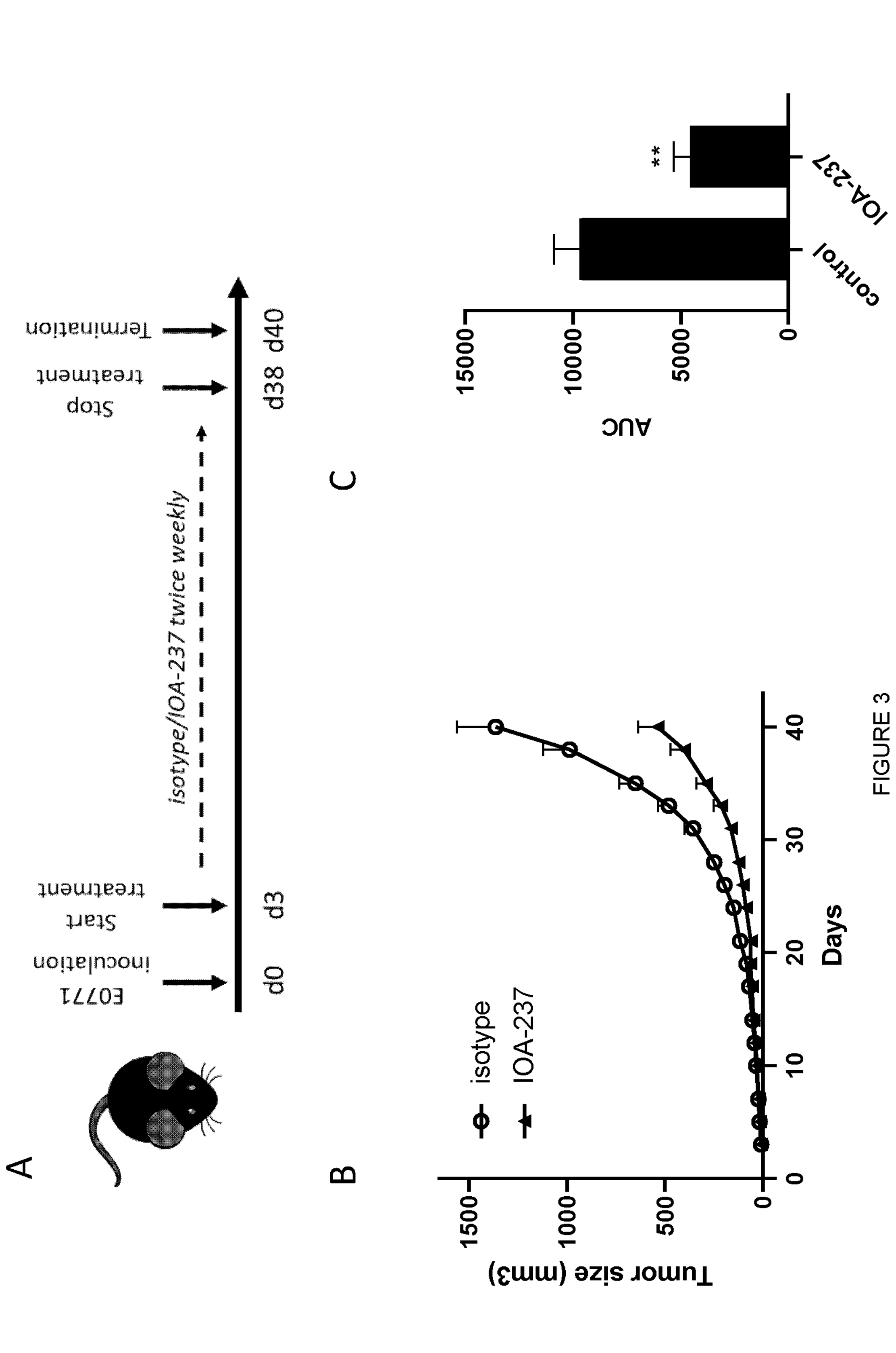
FIG. 3A is a schematic representation of the experimental protocol used to assess the therapeutic utility of IOA-237 in a murine model of triple negative breast cancer (TNBC).
FIG. 3B shows aggregate tumour growth data over a period of 40 days in E0177 tumour-bearing mice (n=10, mean±SEM), treated using isotype control antibody or IOA-237.
FIG. 3C shows tumour growth data quantified as area under the curve (AUC). Data is n=10, mean±SEM. Unpaired T test P is 0.0019

In a murine model of triple-negative breast cancer (TNBC), n=10 C57BL/6 mice were inoculated (orthotropic) with 1×10ˆ6 E0771 medullary breast adenocarcinoma cells. Three days post-inoculation, animals were administered 10 mg/kg IOA-237 (or isotype control antibody) twice per week. Tumour growth was measured at 3-, 10-, 20-, 30- and 40-days post-inoculation. A schematic diagram illustrating this experimental protocol is presented in FIG. 3A. Demonstrating the therapeutic efficacy of IOA-237 in TNBC, a substantial decrease in tumour growth was observed in E0177 tumour-bearing mice treated with IOA-237, when compared to animals treated using an isotype control antibody (FIG. 3B). The observed decrease in tumour growth was quantified as area under the curve (AUC) (FIG. 3C).

Figure 4:
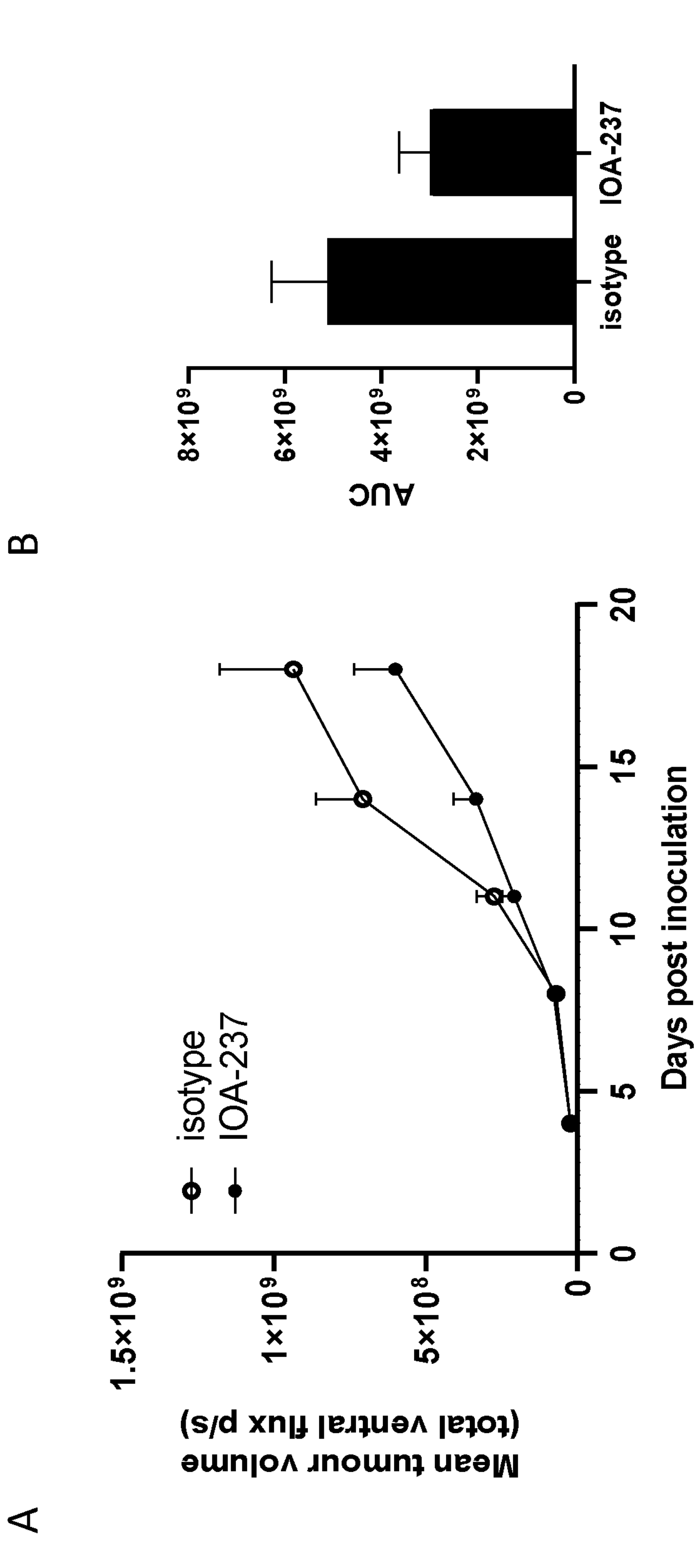
FIG. 4A shows aggregate tumour growth data over a period of 20 days in MuPrime™ tumour-bearing mice (n=9, mean±SEM), treated using isotype control antibody or IOA-237.
FIG. 4B shows tumour growth data quantified as area under the curve (AUC). Data is n=9, mean±SEM.

In a model of pancreatic cancer, n=9 MuPrime™ C57BL/6 mice were inoculated (orthotropic) with 1×10≢cells from the tumour homograft cell line mPA6115. Four days post-inoculation, animals were administered 10 mg/kg IOA-237 (or isotype control antibody). Tumour growth was measured at 5-, 10-, 15- and 20-days post-inoculation. Demonstrating the therapeutic efficacy of IOA-237 in pancreatic cancer, a decrease in tumour growth was observed in MuPrime™ tumour-bearing mice treated with IOA-237, when compared to animals treated using an isotype control antibody (FIG. 4A). The observed decrease in tumour growth was quantified as area under the curve (AUC) (FIG. 4B).

In combination, these data demonstrate that the novel recombinant anti-CD73 antibody IOA-237 possesses favourable pharmacokinetic properties in vivo, and is a therapeutically efficacious oncolytic agent in preclinical models of cancer

Tables

TABLE 1

Data comparing the efficacy of IOA-237 against competitor anti-CD73 antibodies

| | % Inhibition of CD73 (biochemical assay) | | % internalisation of membrane-bound CD73 | | % Inhibition of CD73 (cell-based assay) | |
|---|---|---|---|---|---|---|
| Antibody | Human | Mouse | Human | Mouse | Membrane-bound | soluble |
| IOA-237 | 63.24 | 50.18 | 55.96 | 70.61 | 40.72 | 61.47 |
| MEDI9447 | 42.28 | 49.07 | 58.05 | 70.94 | 42.00 | 39.99 |
| BMS-986179 | 20.03 | 21.29 | 61.73 | 7.14 | 29.90 | 10.39 |
| IPH53 | 91.30 | 17.75 | 47.53 | 06.46 | 68.21 | 77.14 |

TABLE 2

Receptor internalisation assay.

| | Human % Inh | | Murine % Inh | |
|---|---|---|---|---|
| TDL ID | n = 1 | n = 2 | n = 1 | n = 2 |
| ABY001 | 19.77 | 26.08 | 2.73 | 9.85 |
| ABY005 | 11.9 | 30.53 | 4.72 | 15.34 |
| ABY006 | 11.51 | 10.92 | 7.01 | 34.3 |
| ABY007 | 12.61 | 18.56 | 7.55 | 14.37 |
| ABY010 | 12.04 | 25.84 | 8.95 | 11.92 |
| ABY011 | 44.41 | 67.5 | 65.79 | 75.43 |
| ABY012 | 8.24 | 26.39 | 3.52 | 7.99 |
| ABY014 | 16.59 | 27.73 | 8.65 | 7.71 |
| ABY015 | 8.68 | 19.49 | 6.42 | 9.18 |
| ABY021 | 8.01 | 23.64 | 4.9 | 8.09 |
| ABY023 | 20.38 | 16.58 | 5.13 | 6.26 |
| ABY033 | 4.25 | 25.18 | 4.94 | 5.82 |
| ABY035 | 27.84 | 43.53 | 9.34 | 9.73 |
| ABY038 | 6.78 | 19.2 | 4.53 | 11.4 |
| ABY040 | 11.1 | 13.85 | 8.46 | 9.05 |
| ABY043 | 9.06 * | 13.69 | 1.25 | 4.85 |
| ABY048 | 7.95 * | 19.16 | 3.62 | 3.31 |
| ABY053 | 11.58 * | 44.23 | 7.83 | 6.1 |
| ABY055 | 8 * | 15.87 | 7.67 | 12.11 |
| ABY060 | 8.94 * | 27.97 | 7.91 | 8.78 |
| ABY077 (Innate) | 49.02 | 46.03 | 5.18 | 7.74 |
| ABY078 (MEDI) | 49.94 | 66.15 | 62.45 | 79.42 |
| ABY079 (BMS) | 8.99 * | 61.73 | 5.18 | 9.09 |
| ABY080 (IgG1) | 9.94 | 12.89 | 1.92 | 15.34 |

* = One plate failed in n = 1 positive control

TABLE 3

Inhibition of membrane-bound CD73 (cell-based assay).

| Antibody | Max % act n = 1 | n = 2 | Mean |
|---|---|---|---|
| ABY77 | 69.5 | 68 | 68.75 |
| ABY11 | 42 | 43 | 42.5 |
| ABY78 | 35.5 | 48 | 41.75 |

TABLE 3-continued

| Inhibition of membrane-bound CD73 (cell-based assay). | | | |
|---|---|---|---|
| Antibody | Max % act n = 1 | n = 2 | Mean |
| ABY35 | 38.8 | 35.7 | 37.25 |
| ABY79 | 30 | 32 | 31 |
| ABY53 | 16.7 | 25 | 20.85 |
| ABY48 | 22.5 | 15.3 | 18.9 |
| ABY33 | 22.5 | 15.2 | 18.85 |
| ABY10 | 15 | 13 | 14 |
| ABY40 | 13 | 10.6 | 11.8 |
| ABY60 | 12 | 11 | 11.5 |
| ABY55 | 3 | 11.7 | 7.35 |
| ABY23 | 7 | 5.1 | 6.05 |
| ABY07 | 3.7 | 5.7 | 4.7 |
| ABY80 | 6.4 | 1 | 3.7 |

TABLE 3-continued

| Inhibition of membrane-bound CD73 (cell-based assay). | | | |
|---|---|---|---|
| Antibody | Max % act n = 1 | n = 2 | Mean |
| IGG1K | — | 3.5 | 3.5 |
| ABY43 | 0.5 | 4.4 | 2.45 |
| ABY15 | 23.5 | Failed Z' | — |
| ABY05 | 19 | Failed Z' | — |
| ABY12 | 18 | Failed Z' | — |
| ABY14 | 13 | Failed Z' | — |
| ABY01 | 11 | Failed Z' | — |
| ABY06 | — | Failed Z' | — |

ABY77 (IPH-53); ABY11 (IOA-237); ABY78 (MEDI-9447); ABY79 (BMS-986179)/

Reference Sequences

DYX$_1$MS
where independently X$_1$ is Y or A
SEQ ID NO: 1 VHCDR1

YISSSSSYTNYADSVKG
SEQ ID NO: 2 VHCDR2

GX$_1$YQYFDY
where independently X$_1$ is Y, F, A or W
SEQ ID NO: 3 VHCDR3

SGSX$_1$SNIGX$_2$NYVX$_3$
where independently
X$_1$ is R or S
X$_2$ is H or S
X$_3$ is S or Y
SEQ ID NO: 4 VLCDR1

X$_1$NX$_2$X$_3$RPS
where independently
X$_1$ is D or R
X$_2$ is D or N
X$_3$ is K or Q
SEQ ID NO: 5 VLCDR2

AAX$_1$DX$_2$X$_3$LX$_4$GWV
where independently
X$_1$ is Y, F, A or W
X$_2$ is D, E or A
X$_3$ is S, T or A
X$_4$ is N, S, Q or A
SEQ ID NO: 6 VLCDR3

DYAMS
SEQ ID NO: 7 VHCDR1 (H07)

DYYMS
SEQ ID NO: 8 VHCDR1 (germlined H07 variant)

GWYQYFDY
SEQ ID NO: 9 VHCDR3 (H07)

SGSRSNIGHNYVS
SEQ ID NO: 10 VLCDR1 (H07)

SGSSSNIGSNYVY
SEQ ID NO: 11 VLCDR1 (germlined H07 variant)

DNDKRPS
SEQ ID NO: 12 VLCDR2 (H07)

RNNQRPS
SEQ ID NO: 13 VLCDR2 (germlined H07 variant)

AAX$_1$DDSLNGWV
where independently
X$_1$ is Y, F, A or W
SEQ ID NO: 14 VLCDR3 (H07 with modifications)

AAX$_1$DDSLSGWV

-continued where independently
$X_1$ is Y, F, A or W
SEQ ID NO: 15 VLCDR3 (germlined H07 with modifications)

AAWDDSLNGWV
SEQ ID NO: 16 VLCDR3 (H07)

$X_1$VQLLESGGGLV$X_2$PGGSLRLSCAASGFTF$X_3$DY$X_4$MSW$X_5$RQAPGKGLEWVSYISSSSSYTNYADSVKGRFTISRDN$X_6$K
N$X_7$LYLQMNSLRAEDTAVYYCARG$X_8$YQYFDYWGQGTLVTVSS
where independently
$X_1$ is Q or E
$X_2$ is Q or K
$X_3$ is G or S
$X_4$ is A or Y
$X_5$ is I or F
$X_6$ is S or A
$X_7$ is T or S
$X_8$ is independently Y, F, A or W
SEQ ID NO: 17 VH QVQLLESGGGLVKPGGSLRLSCAASGFTFGDYAMSWFRQAPGKGLEWVSYISSSSSYTNYADSVKGRFTISRDNAKNSLY
LQMNSLRAEDTAVYYCARG$X_1$YQYFDYWGQGTLVTVSS
where independently $X_1$ is Y, F, A, or W
SEQ ID NO: 18 (germlined H07 VH with modifications)

EVQLLESGGGLVQPGGSLRLSCAASGFTFGDYAMSWFRQAPGKGLEWVSYISSSSSYTNYADSVKGRFTISRDNSKNTLY
LQMNSLRAEDTAVYYCARG$X_1$YQYFDYWGQGTLVTVSS
where independently $X_1$ is Y, F, A, or W
SEQ ID NO: 19 (H07 VH with modifications)

EVQLLESGGGLVQPGGSLRLSCAASGFTFGDYAMSWFRQAPGKGLEWVSYISSSSSYTNYADSVKGRFTISRDNSKNTLY
LQMNSLRAEDTAVYYCARGWYQYFDYWGQGTLVTVSS
SEQ ID NO: 20 (H07 VH)

QSVLTQPPSASGTPGQRVTISCSGS$X_1$SNIG$X_2$NYV$X_3$WYQQLPGTAPKLLIY$X_4$N$X_5$$X_6$RPSGVPDRFSGSKSGTSASLAI
SGLRSEDEADYYCAA$X_7$D$X_8$$X_9$L$X_{10}$GWVFGGGTKLTVL
where independently
$X_1$ is R or S
$X_1$ is R or S
$X_2$ is H or S
$X_3$ is S or Y
$X_4$ is D or R
$X_5$ is D or N
$X_6$ is K or Q
$X_7$ is Y, F, A, or W
$X_8$ is D, E or A
$X_9$ is S, T or A
$X_{10}$ is N, S, Q or A
SEQ ID NO: 21 VL QSVLTQPPSASGTPGQRVTISCSGSSSNIGSNYVYWYQQLPGTAPKLLIYRNNQRPSGVPDRFSGSKSGTSASLAISGLR
SEDEADYYCAA$X_1$D$X_2$$X_3$LSGWVFGGGTKLTVL
where independently
$X_1$ is Y, F, A, or W
$X_2$ is D, E or A
$X_3$ is S, T or A
SEQ ID NO: 22 (germlined H07 VL with modifications)

QSVLTQPPSASGTPGQRVTISCSGSRSNIGHNYVSWYQQLPGTAPKLLIYDNDKRPSGVPDRFSGSKSGTSASLAISGLR
SEDEADYYCAA$X_1$D$X_2$$X_3$LSGWVFGGGTKLTVL
$X_1$ is Y, F, A, or W
$X_2$ is D, E or A
$X_3$ is S, T or A
SEQ ID NO: 23 (H07 VL with modifications)

QSVLTQPPSASGTPGQRVTISCSGSRSNIGHNYVSWYQQLPGTAPKLLIYDNDKRPSGVPDRFSGSKSGTSASLAISGLR
SEDEADYYCAAWDDSLNGWVFGGGTKLTVL
SEQ ID NO: 24 (H07 VL)

GAGGTGCAGCTGTTGGAGTCTGGGGGAGGCTTGGTACAGCCTGGGGGGTCCCTGAGACTCTCCTGTGCAGCCTCTGGATT
CACCTTTGGTGATTATGCTATGAGCTGGTTCCGCCAGGCTCCAGGGAAGGGGCTGGAGTGGGTTTCATACATTAGTAGTA
GTAGTAGTTACACAAACTACGCAGACTCTGTGAAGGGCCGATTCACCATCTCCAGAGACAATTCCAAGAACACGCTGTAT
CTGCAAATGAACAGCCTGAGAGCCGAGGACACTGCCGTGTATTACTGTGCGAGAGGCTGGTACCAATACTTTGACTACTG
GGGCCAGGGTACACTGGTCACCGTGAGCTCA
SEQ ID NO: 25 (H07 VH coding sequence)

CAGTCTGTGCTGACTCAGCCACCCTCAGCGTCTGGGACCCCCGGGCAGAGGGTCACCATCTCATGCTCTGGAAGCAGGTC
CAACATCGGGCATAACTATGTCTCCTGGTATCAGCAGCTCCCAGGAACGGCCCCCAAACTCCTCATCTATGACAATGATA
AGCGACCCTCAGGGGTCCCTGACCGATTCTCTGGCTCCAAGTCTGGCACCTCAGCCTCCCTGGCCATCAGTGGGCTCCGG

-continued

| |
|---|
| TCCGAGGATGAGGCTGATTATTACTGTGCAGCATGGGATGACAGCCTGAATGGTTGGGTGTTCGGCGGAGGAACCAAGCT<br>GACGGTCCTA |
| SEQ ID NO: 26 (H07 VH coding sequence) |

The invention claimed is:

1. An antibody molecule comprising a VH domain and a VL domain;

wherein the VH domain comprises a VHCDR1 of SEQ ID NO: 1, a VHCDR2 of SEQ ID NO: 2, and a VHCDR3 of SEQ ID NO: 3; and wherein the VL domain comprises a VLCDR1 of SEQ ID NO: 4, a VLCDR2 of SEQ ID NO: 5, and a VLCDR3 of SEQ ID NO: 6; and wherein teh antibody molecule binds specifically to CD73.

2. The antibody molecule according to claim 1 wherein the VHCDR1 has amino acid sequence of SEQ ID NO: 7 or SEQ ID NO: 8.

3. The antibody molecule according to claim 1 wherein the VHCDR3 has amino acid sequence of SEQ ID NO: 9.

4. The antibody molecule according to claim 1 wherein the VLCDR1 has amino acid sequence of SEQ ID NO: 10 or SEQ ID NO: 11.

5. The antibody molecule according to claim 1 wherein the VLCDR2 has the sequence of SEQ ID NO: 12 or SEQ ID NO: 13.

6. The antibody molecule according to claim 1 wherein the VLCDR3 has a sequence selected from the group consisting of SEQ ID NOs: 14, 15, and 16.

7. The antibody molecule according to claim 1 wherein the VH domain has a sequence selected from the group consisting of SEQ ID NO: 17 orand a variant thereof of SEQ ID NO: 17.

8. The antibody molecule according to claim 1 wherein the VL domain has a sequence selected from the group consisting of SEQ ID NO: 21 and a variant of SEQ ID NO:21.

9. The antibody according to claim 1 wherein the VH domain comprises a VHCDR1 of SEQ ID NO: 7, a VHCDR2 of SEQ ID NO: 2, and a VHCDR3 of SEQ ID NO: 9 and the VL domain comprises a VLCDR1 of SEQ ID NO: 10, a VLCDR2 of SEQ ID NO: 12, and a VLCDR3 of SEQ ID NO: 16.

10. The antibody according to claim 9 wherein the VH domain comprises the amino acid sequence of SEQ ID NO: 20 or a variant thereof and the VL domain comprises the amino acid sequence of SEQ ID NO: 24, or a variant thereof.

11. A pharmaceutical composition comprising an antibody molecule according to claim 1 and a pharmaceutically acceptable carrier.

12. A nucleic acid encoding an antibody molecule of claim 1.

13. A vector comprising the nucleic acid of claim 12 operably linked to a promoter.

14. A host cell comprising the nucleic acid of claim 12.

15. A method for making an antibody molecule, the method comprising expressing, in a host cell culture, a vector according to claim 13 to produce said antibody molecule; and recovering the antibody molecule from the cell culture.

16. A method of reducing immunosuppression in a tumour and/or inhibiting tumour growth in an individual in need thereof comprising;

administering an effective amount of the antibody molecule according to claim 1 to the individual.

17. A method of treatment of cancer in an individual in need thereof comprising;

administering an effective amount of the antibody molecule according to claim 1 to the individual.

18. A method of detecting the presence of CD73 in a sample, comprising:

(a) contacting a sample containing, or suspected to contain, CD73 with an antibody molecule according to claim 1, and (b) detecting the formation of a complex of the antibody molecule and CD73, thereby detecting the presence of CD73 in the sample.

* * * * *